US011673942B2

(12) United States Patent
Huelsmann et al.

(10) Patent No.: US 11,673,942 B2
(45) Date of Patent: Jun. 13, 2023

(54) FUSION PROTEINS FOR OPHTHALMOLOGY WITH INCREASED EYE RETENTION

(71) Applicant: Hoffmann-La Roche Inc., Little Falls, NJ (US)

(72) Inventors: Michael Huelsmann, Habach (DE); Erhard Kopetzki, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 213 days.

(21) Appl. No.: 17/066,215

(22) Filed: Oct. 8, 2020

(65) Prior Publication Data

US 2021/0024624 A1 Jan. 28, 2021

Related U.S. Application Data

(60) Division of application No. 16/209,575, filed on Dec. 4, 2018, now Pat. No. 10,836,816, which is a continuation of application No. PCT/EP2017/063506, filed on Jun. 2, 2017.

(30) Foreign Application Priority Data

Jun. 6, 2016 (EP) ..................................... 16173166

(51) Int. Cl.
| | | |
|---|---|---|
| *A61K 39/00* | (2006.01) | |
| *A61K 39/395* | (2006.01) | |
| *C07K 16/18* | (2006.01) | |
| *A61K 47/65* | (2017.01) | |
| *A61K 47/68* | (2017.01) | |
| *A61P 27/02* | (2006.01) | |
| *C07K 16/46* | (2006.01) | |
| *C07K 14/78* | (2006.01) | |

(52) U.S. Cl.
CPC .............. *C07K 16/18* (2013.01); *A61K 47/65* (2017.08); *A61K 47/6879* (2017.08); *A61P 27/02* (2018.01); *C07K 16/46* (2013.01); *A61K 2039/505* (2013.01); *C07K 14/78* (2013.01); *C07K 2317/33* (2013.01); *C07K 2317/55* (2013.01); *C07K 2317/622* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly |
| 8,394,378 | B2 | 3/2013 | Kehoe |
| 10,836,816 | B2 | 11/2020 | Huelsmann et al. |
| 2003/0099655 | A1 | 5/2003 | Watkins et al. |
| 2005/0260186 | A1 | 11/2005 | Bookbinder |
| 2006/0104968 | A1 | 5/2006 | Bookbinder |
| 2012/0108795 | A1 | 5/2012 | Kehoe et al. |
| 2014/0220634 | A1 | 8/2014 | Kehoe |
| 2016/0068605 | A1 | 3/2016 | Nemeth |
| 2019/0218282 | A1* | 7/2019 | Dengl ..................... C07K 16/22 |
| 2019/0225676 | A1 | 7/2019 | Huelsmann |

FOREIGN PATENT DOCUMENTS

| | | |
|---|---|---|
| WO | 2008135734 A1 | 11/2008 |
| WO | 2012047583 A2 | 4/2012 |
| WO | 2012047583 A3 | 10/2013 |
| WO | 2014099997 A1 | 6/2014 |
| WO | 2015108998 A2 | 7/2015 |
| WO | 2015108998 A3 | 10/2015 |
| WO | 2015108998 A9 | 6/2016 |

OTHER PUBLICATIONS

Liu et al. Animal models of ocular angiogenesis: from development to pathologies. FASEB J. 31, 4665-4681 (2017) (Year: 2017).*
Edwards et al., The remarkable flexibility of the human antibody repertoire; isolation of over one thousand different antibodies to a single protein, BLyS. J Mol Biol. Nov. 14, 2003;334(1): 103-18. (Year: 2003).*
Lloyd et al., Modelling the human immune response: performance of a 1011 human antibody repertoire against a broad panel of therapeutically relevant antigens. Protein Eng Des Sei. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*
Kanyavuz et al., Breaking the law: unconventional strategies for antibody diversification. Nat Rev Immunol. Jun. 2019; 19(6):355-368. (Year: 2019).*
Nakaizumi et al. Measurement of serum and vitreous concentrations of anti-type II collagen antibody in diabetic retinopathy. Clinical Ophthalmology 2015:9 543-547. (Year: 2015).*
Ikeda et al. The role of tryptase and anti-type II collagen antibodies in the pathogenesis of idiopathic epiretinal membranes. Clinical Ophthalmology 2015:9 1181-1186. (Year: 2015).*

(Continued)

*Primary Examiner* — Maher M Haddad
(74) *Attorney, Agent, or Firm* — Morrison & Foerster LLP

(57) ABSTRACT

The combination of a first binding site specifically binding to a target associated with an eye disease and a second binding site specifically binding to a target influencing the retention in the eye a multispecific binder provides for improved intravitreal retention compared to a monospecific binder. The second binding site specifically binds to a compound/molecules found in the extracellular matrix (ECM) in vitreous humor/retina. This compound of the extracellular matrix has to be present in amounts allowing a sufficient loading/dose of the drug to be bound. It has been found that collagen, especially collagen II, is a suitable compound in the ECM in the vitreous humor for this purpose. Thus, herein is reported a multispecific binder comprising a first binding site specifically binding to a therapeutic ocular target, and a second binding site specifically binding to collagen II.

7 Claims, 2 Drawing Sheets

Specification includes a Sequence Listing.

(56) References Cited

OTHER PUBLICATIONS

Peter Lundh von Leithner, Daiju Iwata, Y. Ng, Jorg Regula, Guido Hartmann, David T Shima; Bispecific anti-VEGF/ANG2 antibody exhibits superior efficacy to VEGF monotherapy in a model of spontaneous CNV. Invest. Ophthalmol. Vis. Sci. 2014;55(13):2356. (Year: 2014).*

Angi, M. et al. (2012). "Proteomic Analysis of the Vitreous Humour," Hindawi Publishing Corporation Mediators of Inflammation Article ID 148039, pp. 1-7.

Aretz, S. et al. (2013). "In-Depth Mass Spectrometric Mapping of the Human Vitreous Proteome," Proteome Science 11(22):1-10.

Bishop, P. et al. (1996). "The Biochemical Structure of Mammalian Vitreous," Eye 10:664-670.

Bishop, P.N. et al. (2000). "Structural Macromolecules and Supramolecular Organisation of the Vitreous Gel," Progress in Retinal and Eye Research 19(3):323-344.

Bishop, P.N. et al. (2002). "The Role of the Posterior Ciliary Body in the Biosynthesis of Vitreous Humour," Eye 16:454-460.

European Office Action, dated Sep. 15, 2020, for European Patent Application No. 17728816.4, 4 pages.

Favara, D.M. et al. (2014). "VEGF Sticky-Trap: The First Report of a Nonsystemically Acting Angiogenesis Inhibitor," EMBO Molecular Medicine 6(5):577-579.

Garner, A. (1994). "Pathobiology of Ocular Disease. A Dynamic Approach Vascular Diseases," Garner, .A, Klintworth GK Eds., 2nd edition, NY: Marcel Dekker, 1625-1710.

Geisse, S. et al. (Nov. 1996). "Eukaryotic Expression Systems: A Comparison," Protein Expr. Purif. 8 (3):271-282.

International Preliminary Report on Patentability, dated Dec. 11, 2018, for PCT Application No. PCT/EP2017/063506, Filing Jun. 2, 2017, 5 pages.

International Search Report and Written Opinion, dated Aug. 8, 2017, for PCT Application No. PCT/EP2017/063506, filed Jun. 2, 2017, 8 pages.

Kaufman, R.J. (2000). "Overview of Vector Design for Mammalian Gene Expression," Molecular Biotechnology 16:151-160.

Kleinberg, T.T. et al. (Jul.-Aug. 2011). "Vitreous Substitutes: A Comprehensive Review," Survey of Ophthalmology 56(4):300-323.

Makrides, S.C. (Nov. 1999). "Components of Vectors for Gene Transfer and Expression in Mammalian Cells," Protein Expr. Purif 17(2):183-202.

Michael, I.P. et al. (2014). "Local Acting Sticky-Trap Inhibits Vascular Endothelial Growth Factor Dependent Pathological Angiogenesis in the Eye," EMBO Molecular Medicine 6(5):604-623.

Nandakumar, K.S. et al. (2003). "Induction of Arthritis by Single Monoclonal IgG Anti-Collagen Type II Antibodies and Enhancement of Arthritis in Mice Lacking Inhibitory FcyRIIB," European Journal Immunology 33(8):2269-2277.

Non-Final Office Action, dated Mar. 6, 2020, for U.S. Appl. No. 16/209,575, filed Dec. 4, 2018, 7 pages.

Ponsioen, T.I. et al. (2008). "Collagen Distribution in the Human Vitreoretinal Interface," Investigative Ophthalmology & Visual Science 49(9):4089-4095.

Ritter, M.R. et al. (2006). "Myeloid Progenitors Differentiate Into Microglia and Promote Vascular Repair In a Model of Ischemic Retinopathy," J. of Clinical Investigation 116(12):3266-3276.

Russelakis-Cameiro, M. et al. (1999). "Inflammatory Response and retinal Ganglion Cell Degeneration Following Intraocular Injection of ME7," Neuropathology and Applied Neurobiology 25:196-206.

Theocharis, A.D. et al. (2002). "Occurrence and Structural Characterization of Versican-Like Proteoglycan in Human Vitreous," Biochimie 84(12):1235-1241.

Ulrich, J.N. et al. (2008). "Components of the Fibrinolytic System In The Vitreous Body in Patients With Vitreoretinal Disorders," Clinical & Experimental Ophthalmology 36:431-436.

Uysal, H. et al. (2008, e-pub. Feb. 1, 2008). "The Crystal Structure of the Pathogenic Collagen Type II-Specific Mouse Monoclonal Antibody CIIC1 Fab: Structure To Function Analysis," Molecular Immunology 45(8):2196-2204.

Weatherill, E.E. et al. (2012, e-pub. May 14, 2012). "Towards a Universal Disulphide Stabilized Sing Chain Fv Format: Importance of Interchain Disulphide Bond Location and vL-vH Orientations," Protein Engineering, Design & Selection 25(7):321-329.

Werner, R.G. et al. (Aug. 1998). "Appropriate Mammalian Expression Systems for Biopharmaceuticals," Arzneimittelforschung 48:870-880.

Wray, S.H. et al. (1976). "Experimental Allergic Encephalomyelitis," Arch. Neurol. 33:183-185.

Wu, C.W. et al. (2004). "Identification and Localization of Major Soluble Vitreous Proteins in Human Ocular Tissue," American Journal Of Ophthalmology 137:655-661.

Xu, Y. et al. (2004, e-pub. Apr. 30, 2004). "Two Monoclonal Antibodies to Precisely the Same Epitope of Type II Collagen Select Non-Crossreactive Phage Clones By Phage Display: Implications For Autoimmunity and Molecular Mimicry," Molecular Immunology 41(4):411-419.

Alhayek, A. et al. (Apr. 18, 2015). "Corneal Collagen Crosslinking in Keratoconus and Other Eye Disease," International Journal of Ophthalmology 8(2):407-418.

* cited by examiner

FUSION PROTEINS FOR OPHTHALMOLOGY WITH INCREASED EYE RETENTION

CROSS-REFERENCE TO RELATED APPLICATIONS

This application is a divisional application of U.S. patent application Ser. No. 16/209,575, filed on Dec. 4, 2018, which is a continuation of International Application No. PCT/EP2017/063506, having an international filing date of Jun. 2, 2017, which claims the priority benefit under 35 U.S.C. § 119 to European Patent Application No. 16173166.6, filed on Jun. 6, 2016, the entire contents of each of which are incorporated herein by reference.

FIELD OF THE INVENTION

The current invention is in the field of ophthalmologic diseases and their treatment. Herein are reported fusion proteins, i.e. multifunctional binders, for intraocular/intravitreal application that are suitable for the treatment of ophthalmologic diseases. Due to their multifunctionality the fusion protein can bind to an eye retention target and a therapeutic target.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392047210SEQLIST.TXT, date recorded: Oct. 6, 2020, size: 61 KB).

BACKGROUND OF THE INVENTION

One of the factors resulting in the clearance of therapeutic molecules from the eye is diffusion. The diffusive properties of a therapeutic molecule are mainly determined by its size eventually in combination with Fc-receptor binding. After clearance from the eye the therapeutic molecule can be found in the systemic circulation.

Kleinberg, T. T. et al. (Surv. Ophthalmol. 56 (2011) 300-323) provided a review of vitreous substitutes. Permanent vitreous replacement has been attempted with collagen, hyaluronic acid, hydroxypropyl methyl cellulose, and natural hydrogel polymers. None, however, have proven to be clinically viable.

Favara, D. M. and Harris, A. L. (EMBO Mol. Med. 6 (2014) 577-579) disclosed a VEGF sticky-trap as non-systemically acting angiogenesis inhibitor with local inhibition of angiogenesis without detectable systemic side effects. The VEGF sticky-trap is a dimer of a polypeptide comprising VEGF receptor 1 domain 2, VEGF receptor 2 domain 3, a CH3 domain and heparin-binding domain (parts from exons 6, 7 and 8).

Ponsioen, T. L., et al. (Invest. Ophthal. Vis. Sci. 49 (2008) 4089-4095) disclosed the collagen distribution in the human vitreoretinal interface. Retinectomy samples expressed mRNA of all tested collagen types.

WO 2008/135734 discloses a composition comprising an antibody or fragment thereof against oxidized collagen II in which the antibody or fragment is conjugated to a pharmaceutically active moiety.

Uysal, H., et al. (Mol. Immunol. 45 (2008) 2196-2204) disclosed the crystal structure of the pathogenic collagen type II-specific monoclonal antibody CIIC1 Fab.

Nandakumar, K-S., et al. (Eur. J. Immunol. 33 (2003) 2269-2277) disclosed the induction of arthritis by single monoclonal IgG anti-collagen type H antibodies and enhancement of arthritis in mice lacking inhibitory FcgammaRIIb.

Xu, Y., et al. (Mol. Immunol. 41 (2004) 411-419) disclosed that two monoclonal antibodies to precisely the same epitope of type II collagen select non-cross-reactive phage clones by phage display.

WO 2012/047583 discloses antibodies binding human collagen II.

SUMMARY OF THE INVENTION

The current invention is directed to anti-human collagen II antibodies.

Disclosed herein is an anti-human collagen II antibody comprising the six CDRs determined according to Kabat of/as in
  a) SEQ ID NO: 09 and SEQ ID NO: 10, or
  b) SEQ ID NO: 12 and SEQ ID NO: 13, or
  c) SEQ ID NO: 15 and SEQ ID NO: 16.

In one embodiment the antibody comprises a heavy chain variable domain and a light chain variable domain of
  a) SEQ ID NO: 09 and SEQ ID NO: 10, or
  b) SEQ ID NO: 12 and SEQ ID NO: 13, or
  c) SEQ ID NO: 15 and SEQ ID NO: 16.

In one embodiment the antibody is a scFv.

Herein is disclosed as an aspect an antibody binding to the same epitope as an antibody comprising a heavy chain variable domain and a light chain variable domain of
  a) SEQ ID NO: 09 and SEQ ID NO: 10, or
  b) SEQ ID NO: 12 and SEQ ID NO: 13, or
  c) SEQ ID NO: 15 and SEQ ID NO: 16.

Herein is disclosed as an aspect a pharmaceutical formulation comprising the antibody as disclosed herein and optionally a pharmaceutically acceptable excipient.

In one embodiment the pharmaceutical formulation is for use in the treatment of ocular vascular diseases.

Herein is disclosed as an aspect the antibody as disclosed herein for use as a medicament.

In one embodiment the use is for the treatment of ocular vascular diseases.

Herein disclosed as an aspect is the use of the antibody as disclosed herein in the manufacture of a medicament.

In one embodiment the use is for the manufacture of a medicament for the treatment of ocular vascular disease.

Herein is disclosed as an aspect the antibody as disclosed herein for use in the treatment of ocular vascular disease.

Herein is disclosed as an aspect a method of treatment of a patient suffering from an ocular vascular disease by administering an antibody as disclosed herein to a patient in the need of such treatment.

The current invention reports fusion proteins having at least two binding sites, whereof one specifically binds to collagen II.

It has been found that by combining a first binding site that specifically binds to a target associated with an eye disease and a second binding site that specifically binds to a target influencing the retention in the eye (eye retention target) a multispecific binder can be provided with improved intravitreal retention compared to a molecule not having the binding specificity to the eye retention target. The second binding site specifically binds to a compound or molecule found in the extracellular matrix (ECM) in vitreous humor or the retina. This compound of the extracellular matrix has to be present in amounts allowing a sufficient loading and thereby dosing of the multispecific binder. It has been found that collagen, especially collagen II, is a suitable compound in the ECM in the vitreous humor for this purpose.

Such a multispecific binder can be produced recombinantly as (recombinant) fusion protein.

Thus, disclosed herein as an aspect is a fusion protein comprising
- a first binding site specifically binding to a first antigen, and
- a second binding site specifically binding to a compound present in the extracellular matrix of the vitreous humor.

In one embodiment the compound present in the extracellular matrix of the vitreous humor is a collagen. In one embodiment the collagen is collagen II.

In one embodiment the first antigen is related to an ocular vascular disease.

Also disclosed herein as an aspect is a fusion protein comprising
- a first binding site specifically binding to a first antigen, and
- a second binding site specifically binding to collagen II.

In one embodiment the fusion protein comprises
- a first binding site specifically binding to a first antigen,
- a second binding site specifically binding to collagen II, and
- a third binding site specifically binding to a second antigen.

In one embodiment of all aspects as disclosed herein collagen II is human collagen II.

In one embodiment human collagen II has the amino acid sequence of SEQ ID NO: 17 or 18 or 19.

In one embodiment of all aspects as disclosed herein each of the binding sites is selected independently of each other from the group consisting of antibody binding sites, antibody fragments, anticalin, DARPIN, receptor ligand or binding fragment thereof, receptor or binding fragment thereof, and tetranectin domain.

In one embodiment of all aspects as disclosed herein each of the binding sites is independently of each other an antibody binding site or an antibody fragment. In one embodiment each of the binding sites is a pair of an antibody heavy chain variable domain and an antibody light chain variable domain.

In one embodiment of all aspects as disclosed herein the first binding site is comprised in a first polypeptide and the second binding site is comprised in a second polypeptide, wherein the first polypeptide is conjugated or fused to the second polypeptide either directly or via a peptidic linker or via a disulfide bond.

In one embodiment of all aspects as disclosed herein the first binding site is comprised in a first polypeptide, the second binding site is comprised in a second polypeptide and the third binding site is comprised in a third polypeptide, wherein the first polypeptide and the third polypeptide form an antibody or antibody fragment and the antibody or antibody fragment is conjugated to the second polypeptide either directly or via a peptidic linker or a disulfide bond.

In one embodiment of all aspects as disclosed herein the first polypeptide, the second polypeptide and the third polypeptide are selected independently of each other from the group consisting of scFv, dsscFv, Fab, dsFab, CrossFab, monobody, and VHH (sc=single chain, ds=disulfide-stabilized). In one embodiment one of the polypeptides is a Fab or a dsFab and the other polypeptide is a scFv or dsscFv and the polypeptides are conjugated via a peptidic linker. In one embodiment two of the polypeptides are Fabs or dsFabs and the other polypeptide is a scFv or dsscFv and the polypeptides are conjugated via a peptidic linker.

In one embodiment of all aspects as disclosed herein the fusion protein comprises
- as first binding site a Fab specifically binding to a first antigen,
- as second binding site a scFv specifically binding to collagen II, and
- a peptidic linker,
- wherein the Fab is conjugated by a peptide bond at one of its C-termini to the N-terminus of the peptidic linker and the scFv is conjugated by a peptide bond at its N-terminus to the C-terminus of the peptidic linker.

In one embodiment of all aspects as disclosed herein the fusion protein comprises
- a first binding site specifically binding to a first antigen,
- as second binding site a scFv specifically binding to collagen II,
- a third binding site specifically binding to a second antigen, and
- a peptidic linker,
- wherein the combined first and third binding sites are conjugated by a peptide bond at their C-terminus to the N-terminus of the peptidic linker and the scFv is conjugated by a peptide bond at its N-terminus to the C-terminus of the peptidic linker.

In one embodiment of all aspects as disclosed herein the combined first and third binding sites are within/are at least a F(ab')$_2$ or a diabody or a BITE or a tandAb or a DART.

In one embodiment of all aspects as disclosed herein the first antigen and/or the second antigen is a therapeutic ocular target/is related to an ocular vascular disease.

In one embodiment of all aspects as disclosed herein the first antigen and/or the second antigen are independently of each other selected from the group consisting of ANG2, VEGF, PDGF-B, and IL-1beta.

In one embodiment of all aspects as disclosed herein the first antigen and/or the second antigen are different antigens selected from the group consisting of ANG2, VEGF, PDGF-B, and IL-1beta.

In one embodiment the scFv specifically binding to collagen II comprises
a) a heavy chain variable domain with the amino acid sequence of SEQ ID NO: 09 and a light chain variable domain of SEQ ID NO: 10, or
b) a heavy chain variable domain with the amino acid sequence of SEQ ID NO: 12 and a light chain variable domain of SEQ ID NO: 13, or
c) a heavy chain variable domain with the amino acid sequence of SEQ ID NO: 15 and a light chain variable domain of SEQ ID NO: 16.

In one embodiment of all aspects as disclosed herein the scFv specifically binding to collagen II comprises a heavy chain variable domain with the amino acid sequence of SEQ ID NO: 12 and a light chain variable domain of SEQ ID NO: 13.

In one embodiment of all aspects as disclosed herein the scFv specifically binding to collagen II has the amino acid sequence of SEQ ID NO: 11 or SEQ ID NO: 14 or SEQ ID NO: 17.

In one embodiment of all aspects as disclosed herein the scFv specifically binding to collagen II has the amino acid sequence of SEQ ID NO: 14.

In one embodiment of all aspects as disclosed herein the first binding site and the third binding site are Fabs.

In one embodiment of all aspects as disclosed herein the fusion protein comprises
- a Fab specifically binding to ANG2, VEGF, PDGF-B, or IL-1beta,
- a scFv specifically binding to collagen II comprising a heavy chain variable domain with the amino acid sequence of SEQ ID NO: 12 and a light chain variable domain of SEQ ID NO: 13, and
- a peptidic linker,
- whereby the Fab is conjugated by a peptide bond at one of its C-termini to the N-terminus of the peptidic linker and the scFv is conjugated by a peptide bond at its N-terminus to the C-terminus of the peptidic linker.

In one embodiment of all aspects as disclosed herein the fusion protein as a molecular weight of less than 75 kDa.

In one embodiment of all aspects as disclosed herein the fusion protein is devoid of an antibody Fc-region.

Herein is disclosed as an aspect a pharmaceutical formulation comprising the fusion protein as disclosed herein and optionally a pharmaceutically acceptable excipient.

In one embodiment the pharmaceutical formulation is for use in the treatment of ocular vascular diseases.

Herein is disclosed as an aspect the fusion protein as disclosed herein for use as a medicament.

In one embodiment the use is for the treatment of ocular vascular diseases.

Herein disclosed as an aspect is the use of the fusion protein as disclosed herein in the manufacture of a medicament.

In one embodiment the use is for the manufacture of a medicament for the treatment of ocular vascular disease.

Herein is disclosed as an aspect the fusion protein as disclosed herein for use in the treatment of ocular vascular disease.

Herein is disclosed as an aspect a method of treatment of a patient suffering from ocular vascular diseases by administering the fusion protein as disclosed herein to a patient in the need of such treatment.

DETAILED DESCRIPTION OF THE INVENTION

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the generation of derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

I. Definitions

It is herewith expressly stated that the term "comprising" as used herein comprises the term "consisting of". Thus, all aspects and embodiments that contain the term "comprising" are likewise disclosed with the term "consisting of".

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "(intact) antibody" herein is used in the broadest sense and encompasses various antibody structures, including but not limited to monoclonal antibodies.

The term "(intact) antibody" refers to immunoglobulin molecules with varying structures. Intact IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "antibody fragment" denotes a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The terms "antibody binding site" denotes the amino acid residues of an antibody that are responsible for antigen binding. Generally this is a pair of an antibody heavy chain variable domain and light chain variable domain. The antigen-binding site of an antibody comprises amino acid residues from the "hypervariable regions" or "HVRs". "Framework" or "FR" regions are those variable domain regions other than the hypervariable region residues as herein defined. Therefore, the light and heavy chain variable domains of an antibody comprise from N- to C-terminus the regions FR1, CDR1, FR2, CDR2, FR3, CDR3, and FR4 (immunoglobulin framework). Especially, the CDR3 region of the heavy chain is the region, which contributes most to antigen binding and defines the antibody.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means a binding affinity ($K_D$) of about $10^{-7}$ M or less, in some embodiments of $10^{-13}$ to $10^{-8}$ M.

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D(k_d/k_a)$.

The term "binding site" denotes any proteinaceous entity that shows binding specificity to a target.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3). HVRs as denoted herein include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those residues identified elsewhere in the specification as being CDR residues.

Unless otherwise indicated, HVR residues and other residues in the variable domain (e.g., FR residues) are numbered herein according to the Kabat EU index numbering system (Kabat et al., supra).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain embodiments, a human antibody is derived from a non-human transgenic mammal, for example a mouse, a rat, or a rabbit. In certain embodiments, a human antibody is derived from a hybridoma cell line. In certain embodiments, a human antibody is derived from a (phage) display library. In certain embodiments, a human antibody is derived from a human B-cell.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one that has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size-exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, B-cell methods, recombinant DNA methods, phage-display methods, and methods utilizing transgenic animals containing all or part of the human immunoglobulin loci.

The term "ocular vascular disease" includes, but is not limited to intraocular neovascular syndromes such as diabetic retinopathy, diabetic macular edema, retinopathy of prematurity, neovascular glaucoma, retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration (see e.g. Garner, A Vascular diseases, In: Pathobiology of ocular disease, A dynamic approach, Garner, A., and Klintworth, G. K., (eds.), 2nd edition, Marcel Dekker, New York (1994), pp. 1625-1710).

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "peptidic linker" as used herein denotes a peptide with amino acid sequences, which is in one embodiment of synthetic origin. A "peptidic linker" represents a linear chain of amino acid residues. This linear chain of amino acid residues has a length of 1 to 30 residues.

In one embodiment the peptidic linker is rich in glycine, glutamine, and/or serine residues. In one embodiment, these residues are arranged e.g. in small repetitive units of up to five amino acids, such as GS (SEQ ID NO: 21), GGS (SEQ ID NO: 22), GGGS (SEQ ID NO: 23), and GGGGS (SEQ ID NO: 24). The small repetitive unit may be repeated for one to five times. At the amino- and/or carboxyl-terminal ends of the multimeric unit up to six additional arbitrary, naturally occurring amino acids may be added.

The peptidic linker is in one embodiment a peptide with an amino acid sequence with a length of up to 30 amino acid residues, in one embodiment with a length of 5 to 20 amino acid residues. In one embodiment the peptidic linker is (GxS)n with G=glycine, S=serine, (x=3, n=2, 3, 4 or 5) or (x=4 and n=2, 3, or 4), in one embodiment with x=3, n=2, in one embodiment with x=4, n=2. This peptidic linker may nevertheless comprise additional glycine and/or serine residues at one or both of its termini.

Other synthetic peptidic linkers are composed of a single amino acid, which is repeated between 10 to 20 times and may comprise at the amino- and/or carboxyl-terminal end up to six additional arbitrary, naturally occurring amino acids.

Besides synthetic GS-rich peptidic linkers also naturally occurring peptidic linker such as IgG hinge, liker of human P-glycoprotein, C-terminal linker of human replicatin protein A, linker of the parathyroid hormone-related protein, can be used.

All peptidic linkers can be encoded by a nucleic acid molecule and therefore can be recombinantly expressed. As the linkers are themselves peptides, the polypeptide connected by the linker are connected to the linker via a peptide bond that is formed between two amino acids.

The term "recombinant" or "recombinantly produced" denotes polypeptides that are prepared, expressed, created or isolated by recombinant means. This includes polypeptides isolated from a host cell such as a NSO or CHO cell or from an animal (e.g. a mouse) that is transgenic or polypeptides expressed using a recombinant expression vector transfected into a host cell.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or Fc-region fusion polypeptides as reported herein are used to delay development of a disease or to slow the progression of a disease.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein are in one preferred embodiment "bivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W. H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "therapeutic ocular target" denotes a molecule involved in an ocular vascular disease.

The term "diabody" denotes a non-covalent dimer of single chain Fv (scFv) fragment that consists of the heavy chain variable (VH) and light chain variable (VL) regions connected by a small peptide linker. Common linkers in scFvs have 14-15 amino acid residues and are between the N- and C-termini of the variable domains. However, using linkers of 3-12 amino acid residues in length will result in the formation of a diabody.

The term "Tandem scFv (taFv)" denotes a molecule wherein two scFv molecules are conjugated through a short linker.

The term "miniantibody or minibody" denotes a bivalent (or bispecific) (scFv)$_2$ produced by association of two scFv molecules through two modified dimerization domains.

The term "tandAb" denotes a tetravalent, bispecific antibody format that consists of two binding sites for each antigen. It consists only of variable immunglobulin-domains, that are connected by linker.

The term "BITE" denotes a bi-specific T-cell engager (BiTEs). These are a class of artificial bispecific monoclonal antibodies that direct a host's immune system, more specifically the T-cells' cytotoxic activity, against cancer cells. BiTEs are fusion proteins consisting of two single-chain variable fragments (scFvs) of different antibodies, or amino acid sequences from four different genes, on a single peptide chain of about 55 kilodaltons. One of the scFvs binds to T-cells via the CD3 receptor, and the other to a tumor cell via a tumor specific molecule.

The term "DART" denotes a molecule consisting of two engineered Fv fragments which have their own VH exchanged with the other one. In detail, the Fv1 comprises a VH from antibody A and a VL from antibody B, while the Fv2 comprises a VH from Ab-B and VL from Ab-A. This inter-exchange of Fv domains releases variant fragments from the conformational constraint by the short linking peptide.

"Collagen" is the main structural protein in the extracellular space in the various connective tissues in animal bodies. As the main component of connective tissue, it is the most abundant protein in mammals making up from 25% to 35% of the whole-body protein content. Depending upon the degree of mineralization, collagen tissues may be rigid (bone), compliant (tendon), or have a gradient from rigid to compliant (cartilage). Collagen, in the form of elongated fibrils, is mostly found in fibrous tissues such as tendons, ligaments and skin. It is also abundant in corneas, cartilage, bones, blood vessels, the gut, intervertebral discs and the dentin in teeth. In muscle tissue, it serves as a major component of the endomysium. Collagen constitutes one to two percent of muscle tissue, and accounts for 6% of the weight of strong, tendinous muscles. The fibroblast is the most common cell that creates collagen.

"Type II collagen" is the basis for articular cartilage and hyaline cartilage. It makes up 50% of all protein in cartilage and 85-90% of collagen of articular cartilage. Type II collagen does form fibrils. This fibrillar network of collagen allows cartilage to entrap the proteoglycan aggregate as well as provide tensile strength to the tissue. Type II collagen is found in cartilage and the vitreous humor of the eye.

II. The Vitreous Humor/Body

The matrix that fills most space in the eye is denoted as vitreous humor/body.

The human vitreous humor is a clear aqueous solution, which fills the posterior compartment of the eye, located between the lens and the retina. It occupies about 80% of the volume of the eyeball and comprises 99% water but has a gel-like structure at birth due to a network of collagen fibrils and large molecules of hyaluronic acid. Its volume is bout 4-5 ml (Beauthier, J. P., (2008) In: De Boeck Université [Ed]. Traite de médecine légale. Bruxelles: 715-725). Vitreous humor contains several low molecular weight solutes including inorganic salts, sugars and ascorbic acid. The total concentration of protein in human vitreous is approximately 1200 µg/ml, of which collagen accounts for 180 µg/ml (see e.g. Aretz, S., et al., Prot. Sci. 11 (2013) 22; Theocharis, A. D., et al., Biochim. 84 (2002) 1237-1243). An average protein concentration of the healthy vitreous humor of 0.5 mg/mL, consisting largely of albumin (60-70%) is reported by Angi, M., et al. (Hindawi Publishing Corporation, Mediators of Inflammation, Volume 2012, Article ID 148039). Further it is reported therein that components of the vitreous humor are globulins, coagulation proteins, complement factors, and low-molecular-weight proteins (Ulrich, J. N., et al., Clin. Exp. Ophthalmol. 36 (2008) 431-436). The ciliary body provides a constant fluid exchange by diffusion, ultrafiltration, and active transport of aqueous fluid into the posterior segment (Bishop, P. N., Eye, 16 (2002) 454-460). Proteins may accumulate in the vitreous by local secretion (e.g., glycoprotein), filtration from blood (e.g., albumin), or diffusion from the surrounding tissues (Wu, C. W., Am. J. Ophthalmol., 137 (2004) 655-661). Because of the close contact between the vitreous and the inner retina, physiological and pathological conditions of the retina affect both the proteome and the biochemical properties of the vitreous humor.

III. Multifunctional Binders for Ophthalmology with Increased Eye Retention

It has been found that by the combination of a first binding site specifically binding to a target associated with an eye disease and a second binding site specifically binding to a target influencing the retention in the eye a multispecific binder can be provided with improved intravitreal retention compared to a monospecific binder. The second binding site specifically binds to a compound/molecules found in the extracellular matrix (ECM) in vitreous humor/retina. This compound of the extracellular matrix has to be present in amounts allowing a sufficient loading/dose of the drug to be bound. It has been found that collagen, especially collagen II, is a suitable compound in the ECM in the vitreous humor for this purpose.

With a long intravitreal half-life less frequent injections are required, with a short half-life in the systemic circulation a low system exposure can be effected, and with the combination of both an increased efficacy and reduced side effects are expected.

A long intravitreal half-life can be achieved by
high molecular weight (IgGs, addition of e.g. PEG to smaller formats such as diabodies, Fabs etc.),
high affinity and avidity to retention target (lower efficient drug concentration results in less frequent dosing),
high thermal stability at 37° C.,
decreasing diffusion of the molecule across vitreous humor and blood retina barrier (BRB),
optimal charge or pI.

Rapid systemic clearance can be achieved by
engineering the Fc-region for reduced FcRn binding,
low(er) molecular weight (Fab, Diabody, DARPINs),
low administered doses (dose also depends on affinity).

The aim of the current invention is to provide a long lasting drug for application into the eye. This reduces the number of application required and likewise the time between the single applications. This can be achieved on the one hand by increasing the does administered at each application or on the other hand by increasing the half-life and durability of the drug in the eye after application.

The invention relates in general to a multispecific binder (i.e. a recombinant fusion protein) comprising
- a first binding site specifically binding to a therapeutic ocular target, and
- a second binding site specifically binding to collagen II.

In one embodiment each of the binding sites is selected independently of each other from the group consisting of an antibody binding site, an anticalin, a DARPIN, a receptor ligand or binding fragment thereof, a receptor or binding fragment thereof, a tetranectin domain.

In one embodiment each of the binding sites is an antibody binding site. In one embodiment each of the binding sites is a (cognate) pair of an antibody heavy chain variable domain and an antibody light chain variable domain.

In one embodiment the first binding site is comprised in a first domain and the second binding site is comprised in a second domain and the first domain is conjugated to the second domain either directly or via a peptidic linker. In one embodiment the first domain and the second domain are selected independently of each other from the group consisting of scFv, dsscFv, Fab, dsFab, CrossFab, monobody, and VHH (sc=single chain, ds=disulfide-stabilized). In one embodiment one of the domains is a Fab or a dsFab and the other domain is a scFv or dsscFv and the domains are conjugated via a peptidic linker.

In one embodiment the multispecific binder is selected from the group consisting of tandem-Fv, diabody, single-chain diabody, disulfide-stabilized diabody, DART, scFv$_2$, Fab-scFv, minibody.

Herein is disclosed a multispecific binder (i.e. a recombinant fusion protein) comprising
- a Fab or scFv comprising a first binding site specifically binding to a therapeutic ocular target,
- a scFv specifically binding to collagen II, and
- a peptidic linker,
- whereby the Fab or the scFv comprising the first binding site is conjugated by a peptide bond at one of its C-termini to the N-terminus of the peptidic linker and the scFv specifically binding to collagene II is conjugated by a peptide bond at its N-terminus to the C-terminus of the peptidic linker.

In one embodiment the therapeutic ocular target is selected from the group consisting of ANG2, VEGF, PDGF-B, IL-1beta.

In one embodiment the multispecific binder is a bispecific binder comprising
- a Fab specifically binding to ANG2, VEGF, PDGF-B, or IL-1beta,
- a scFv specifically binding to collagen II, and
- a peptidic linker,
- whereby the Fab is conjugated by a peptide bond at one of its C-termini to the N-terminus of the peptidic linker and the scFv is conjugated by a peptide bond at its N-terminus to the C-terminus of the peptidic linker.

In one embodiment the multispecific binder is a trispecific binder comprising
- a first binding site specifically binding to ANG2, VEGF, PDGF-B, or IL-1beta,
- a second binding site specifically binding to ANG2, VEGF, PDGF-B, or IL-1beta,
- a scFv specifically binding to collagen II, and
- a peptidic linker,
- whereby the combined first and second binding site are conjugated by a peptide bond at their C-terminus to the N-terminus of the peptidic linker and the scFv is conjugated by a peptide bond at its N-terminus to the C-terminus of the peptidic linker.

In one embodiment the scFv specifically binding to collagen II comprises
a) a heavy chain variable domain with the amino acid sequence of SEQ ID NO: 09 and a light chain variable domain of SEQ ID NO: 10, or
b) a heavy chain variable domain with the amino acid sequence of SEQ ID NO: 12 and a light chain variable domain of SEQ ID NO: 13, or
c) a heavy chain variable domain with the amino acid sequence of SEQ ID NO: 15 and a light chain variable domain of SEQ ID NO: 16.

In one embodiment the scFv specifically binding to collagen II comprises a heavy chain variable domain with the amino acid sequence of SEQ ID NO: 12 and a light chain variable domain of SEQ ID NO: 13.

In one embodiment the scFv specifically binding to collagen II has the amino acid sequence of SEQ ID NO: 11 or SEQ ID NO: 14 or SEQ ID NO: 17.

In one embodiment the scFv specifically binding to collagen II has the amino acid sequence of SEQ ID NO: 14.

In one embodiment the multi specific binder is a bispecific binder comprising
- a Fab specifically binding to ANG2, VEGF, PDGF-B, or IL-1beta,
- a scFv specifically binding to collagen II comprising a heavy chain variable domain with the amino acid sequence of SEQ ID NO: 12 and a light chain variable domain of SEQ ID NO: 13, and
- a peptidic linker,
- whereby the Fab is conjugated by a peptide bond at one of its C-termini to the N-terminus of the peptidic linker and the scFv is conjugated by a peptide bond at its N-terminus to the C-terminus of the peptidic linker.

The intravitreal half-life and durability of a drug can be increased by different means, such as amongst others for example an increase of the hydrodynamic radius of the drug (thereby slowing down the diffusion from the eye), a high affinity of the drug to its target (thereby reducing the dissociation of drug-target complexes), a high (thermal) degradation stability in the eye, and a high injectable dose).

The main factors thought to influencing durability are the dose (an increase of the applicable dose adds positively to durability), the half-life (an increase in half-life adds positively to durability) and the affinity to the target (represented by $K_D$) (an increase in affinity adds positively to durability).

After intravitreal application a large amount of drug has to be bound by the compound of the ECM in the vitreous humor selected for retention of the drug in the eye. The binding kinetic to said compound must allow a sufficient remaining diffusion of drug into retina/choroidea to maintain minimum effective dose (aim: drug concentration above minimum effective dose as long as possible after the intravitreal application).

The "diffusion rate" (dependent on $k_{on}/k_{off}$ towards the compound of the ECM selected for retention of the drug in the eye and on the capacity of the depot in the vitreous humor) has to be equal or slightly higher than elimination rate into systemic circulation.

The "capacity" (=depot size) of the compound of the ECM selected for retention of the drug in the eye has to be high enough. The capacity is dependent on the amount/accessibility of the compound of the ECM selected for retention of the drug in the eye, the number of binding sites thereof, and on the turnover thereof.

The binder-ECM compound-interaction should reduce the diffusion constant and thereby the clearance from the eye of the conjugate. A reduced diffusion rate in vitreous humor is a prerequisite for increased/improved eye retention. The diffusion constant of fluorescently labeled proteins in complex solutions can be determined by Fluorescence Correlation Spectroscopy (FCS; i.e. DLS using fluorescence).

Parameters as concentration, diffusion coefficients and MW can be determined directly from the measurement. The testing of the diffusivity can be performed in an artificial test solution (comprising the compound of the ECM selected for retention of the drug) "representing" the composition of vitreous fluid or directly in vitreous fluid of minipigs.

Fluorescence Correlation Spectroscopy (FCS) analyzes the stochastic movement of fluorescently labeled molecules in an open microscopic volume element irradiated by a focused laser beam. FCS has been successfully applied for the study of molecular interactions in solution. One binding partner is labeled with a fluorophore and incubated with the designated interactor. Upon binding, the MW and hence the diffusional mobility of the labeled complex is altered, which can be quantified by FCS. Titration of the labeled ligand over a constant concentration of binding partner allow determining the affinity of the interaction. Time resolved measurements will give rise to the corresponding rate constants. Thus, a sufficient shift in complex size FCS can be used for the determination of dissociation- and rate constants.

Brownian motion drives the diffusion of fluorescence-labeled molecules through the illuminated detection volume. The photons emitted while passing through the volume element are recorded on ultra-sensitive avalanche photo detectors (APD). The fluctuations are analyzed by treating the recorded photon counts with a mathematical method called autocorrelation and fitting the deduced autocorrelation function to an appropriate biophysical model.

$$J = -D^* dc/dx$$

$$dc/dt = D^* (d^2c)/(dx^2)$$

J: diffusion flux
D: diffusion constant
c: concentration
x: distance
t: time

Compound of the ECM that can be selected for retention of a drug in the eye are potentially insoluble proteins found in the vitreous humor/body, such as, for example, collagen (type II, IX, V/XI, IV etc.), hyaluronic acid (forms structures together with collagen), chondroitin sulfate, and heparin sulfate.

The current invention is directed to a (at least) bispecific binder comprising a first binding site specifically binding to a target for exerting a therapeutic effect and a second binding site specifically binding to a compound of the ECM selected for retention of the (at least) bispecific binder in the eye.

An exemplary binder according to the invention is an anti-digoxigenin binder combined with a second binding specificity directed against a compound of the ECM selected for retention of the drug in the eye.

Different constructs have been tested in vitro and in vivo:

as reference:
the anti-digoxigenin antibody Fab (denoted as FAB in the following),
the anti-digoxigenin antibody Fab conjugated to a PEG residue of 20 kDa (denoted as FAB-PEG in the following), as bispecific binder/fusion protein:
the anti-digoxigenin antibody Fab conjugated to a heparin-binding domain (human VEGF fragment comprising residues 111-165, denoted as FAB-HBD in the following),
the anti-digoxigenin antibody Fab conjugated to three different anti-collagen II antibody scFv (denoted as FAB-COLL-I (SEQ ID NO: 9 (VH), 10 (VL) and 11 (scFv)), FAB-COLL-II (SEQ ID NO: 12 (VH), 13 (VL) and 14 (scFv)), FAB-COLL-III (SEQ ID NO: 15 (VH), 16 (VL) and 17 (scFv) in the following, which differ in the binding kinetic).

In a minipig study the concentration of the different constructs was determined in vitreous, retina and choroid at 168, 336 and 672 h after intravitreal injection (d0) of a 500 nM solution of the respective construct.

In the vitreous the following time-dependent concentrations have been determined:

|  | 168 h (pmol/g) | 336 h (pmol/g) | 672 h (pmol/g) |
| --- | --- | --- | --- |
| FAB | 82.5 | 53.6 | 6.7 |
| FAB-PEG | 128.6 | 93.3 | 32.5 |
| FAB-HBD | 45.2 | 10.3 | 2.1 |
| FAB-COLL-I | 165.6 | 59.2 | 10.4 |
| FAB-COLL-II | 171.0 | 58.5 | 19.6 |
| FAB-COLL-III | 149.3 | 62.0 | 11.1 |

In the retina the following time-dependent concentrations have been determined:

|  | 168 h (pmol/g) | 336 h (pmol/g) | 672 h (pmol/g) |
| --- | --- | --- | --- |
| FAB | 85.9 | 17.6 | 5.6 |
| FAB-PEG | 50.3 | 43.6 | 5.4 |
| FAB-HBD | 72.5 | 12.6 | 1.1 |
| FAB-COLL-I | 78.2 | 52.6 | 6.7 |
| FAB-COLL-II | 101.3 | 67.7 | 13.6 |
| FAB-COLL-III | 68.2 | 41.6 | 6.6 |

In the choroid the following time-dependent concentrations have been determined:

|  | 168 h (pmol/g) | 336 h (pmol/g) | 672 h (pmol/g) |
| --- | --- | --- | --- |
| FAB | 29.6 | 21.4 | 2.0 |
| FAB-PEG | 54.8 | 34.4 | 23.9 |
| FAB-HBD | 60.2 | 13.1 | 1.6 |
| FAB-COLL-I | 64.2 | 51.7 | 5.4 |
| FAB-COLL-II | 68.2 | 41.6 | 6.6 |
| FAB-COLL-III | 129.5 | 37.8 | 7.2 |

The different collagen scFvs have the following in vitro characteristics:

The half-life of the different constructs in the different compartments (tissues) of the eye is shown in FIG. 1.

The exposure of different compartments (tissues) of the eye with respect to the different constructs is shown in FIG. 2.

The characteristic parameters the constructs were determined in vivo in minipig and in vitro using BIAcore as well as in an artificial diffusion test solution. The data is shown in the following table.

| | $K_D$ (nM) porcine/ human collagen II | diffusion rate FCS (increase in PBS comprising ECM compound at equimolar concentration compared to PBS alone) | diffusion rate FCS (increase in vitreous fluid compared to PBS) |
|---|---|---|---|
| FAB | n.a. | 100% | 100% |
| FAB-PEG | n.a. | +65-100% | +70-100% |
| FAB-HBD (40 nM) | n.a. | +25% | +35% |
| FAB-COLL-I (2 nM) | 56/30 | +180% | +35-130% |
| FAB-COLL-II (8 nM) | 50/15 | +260% | +140-310% |
| FAB-COLL-III (8 nM) | 342/180 | +40% | +30-85% |

| | concentration (nM) | diffusion time vitreous fluid (micro-sec) | diffusion time PBS (micro-sec) |
|---|---|---|---|
| FAB | 8 | 270 | 267 |
| FAB-COLL-I | 2 | 632 | 477 |
| FAB-COLL-II | 8 | 1113 | 347 |
| FAB-COLL-III | 8 | 497 | 390 |

For FAB-COLL-II a 3.2 times increased diffusion time (i.e. a reduced diffusion) has been found in VF, and a 2.7 times increased diffusion time in PBS supplemented with collagen (same FAB-COLL-II concentration).

| | $t_{1/2}$ vitreous (h) | C0 estimate (nM) |
|---|---|---|
| FAB | 135 | 196 |
| FAB-PEG | 249 | 205 |
| FAB-HBD (40 nM) | 118 | 121 |
| FAB-COLL-I (8 nM) | 125 | 421 |
| FAB-COLL-II (2 nM) | 169 | 341 |
| FAB-COLL-III (8 nM) | 134 | 355 |

The multispecific binder/fusion protein as disclosed herein
- supports long intravitreal half-life and short systemic half-life to allow for infrequent dosing and to minimize/rule out systemic toxic effects,
- has vitreous body retention resulting in slower release from the eye, low systemic and less systemic toxicity,
- has increased affinity to the selected ECM compounds leading to lower efficient drug concentration, which may result in less frequent dosing,
- has a specific vitreous body retention moiety leading to long intravitreous half-life,
- has a low molecular weight format combining a vitreous body retention moiety to compensate fast diffusion across vitreous body and blood retinal barrier,
- is a low molecular weight format most feasible for use in eye device,
- by the addition of a third specificity may lead to even higher efficacy,
- when comprising an Fc-region is a high MW format with shortened systemic half-life due to 'silent' Fc part, which does not bind to FcRn.

In one aspect, the invention provides isolated antibodies that bind to human collagen II.

In certain embodiments, the anti-human collagen II antibody has a diffusion time in vitreous fluid of minipigs in micro-seconds at 8 nM concentration of more than 750, in one embodiment of more than 1000.

In certain embodiments, the anti-human collagen II antibody also specifically binds to porcine collagen II.

In certain embodiments, the anti-human collagen II antibody has a $K_D$ value for binding to porcine collagen II of less than 400 nM at a concentration of 8 nM. In one embodiment the $K_D$ is less than 100 nM.

In certain embodiments, the anti-human collagen II antibody has a $K_D$ value for human collagen II of less than 200 nM. In one embodiment the $K_D$ is less than 50 nM.

In certain embodiments, the anti-human collagen II antibody has a half-live in the minipig vitreous of more than 150 hours.

In certain embodiments, the anti-human collagen II antibody has an estimated C0 in minipig of more than 200 nM. In one embodiment the C0 is more than 300 nM.

In one aspect, the invention provides an antibody comprising at least one, at least two, or all three VH HVR determined according to Kabat of SEQ ID NO: 09.

In one aspect, the invention provides an antibody comprising at least one, at least two, or all three VH HVR determined according to Kabat of SEQ ID NO: 12.

In one aspect, the invention provides an antibody comprising at least one, at least two, or all three VH HVR determined according to Kabat of SEQ ID NO: 15.

In one aspect, the invention provides an antibody comprising at least one, at least two, or all three VL HVR determined according to Kabat of SEQ ID NO: 10.

In one aspect, the invention provides an antibody comprising at least one, at least two, or all three VL HVR determined according to Kabat of SEQ ID NO: 13.

In one aspect, the invention provides an antibody comprising at least one, at least two, or all three VL HVR determined according to Kabat of SEQ ID NO: 16.

In another aspect, an antibody of the invention comprises (a) a VH domain comprising at least one, at least two, or all three VH HVR sequences determined according to Kabat of SEQ ID NO: 09; and (b) a VL domain comprising at least one, at least two, or all three VL HVR sequences determined according to Kabat of SEQ ID NO: 10.

In another aspect, an antibody of the invention comprises (a) a VH domain comprising at least one, at least two, or all three VH HVR sequences determined according to Kabat of SEQ ID NO: 12; and (b) a VL domain comprising at least one, at least two, or all three VL HVR sequences determined according to Kabat of SEQ ID NO: 13.

In another aspect, an antibody of the invention comprises (a) a VH domain comprising at least one, at least two, or all three VH HVR sequences determined according to Kabat of SEQ ID NO: 15; and (b) a VL domain comprising at least one, at least two, or all three VL HVR sequences determined according to Kabat of SEQ ID NO: 16.

In any of the above embodiments, an anti-human collagen II antibody is humanized. In one embodiment, an anti-human collagen II antibody comprises HVRs as in any of the above embodiments, and further comprises an acceptor human framework, e.g. a human immunoglobulin framework or a human consensus framework.

In another aspect, an anti-human collagen II antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 09. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human collagen II antibody comprising that sequence retains the ability to bind to human collagen II. In certain embodiments, a total of 1 to 10 amino acids have been substituted, inserted and/or deleted in SEQ ID NO: 09. In certain embodiments, substitutions, insertions, or deletions occur in regions outside the HVRs (i.e., in the FRs). Optionally, the anti-human collagen II antibody comprises the VH sequence in SEQ ID NO: 09, including post-translational modifications of that sequence.

In another aspect, an anti-human collagen II antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 12. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human collagen II antibody comprising that sequence retains the ability to bind to human collagen II. In certain embodiments, a total of 1 to 10 amino acids have been substituted, inserted and/or deleted in SEQ ID NO: 12. In certain embodiments, substitutions, insertions, or deletions occur in regions outside the HVRs (i.e., in the FRs). Optionally, the anti-human collagen II antibody comprises the VH sequence in SEQ ID NO: 12, including post-translational modifications of that sequence.

In another aspect, an anti-human collagen II antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 15. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human collagen II antibody comprising that sequence retains the ability to bind to human collagen II. In certain embodiments, a total of Ito 10 amino acids have been substituted, inserted and/or deleted in SEQ ID NO: 15. In certain embodiments, substitutions, insertions, or deletions occur in regions outside the HVRs (i.e., in the FRs). Optionally, the anti-human collagen II antibody comprises the VH sequence in SEQ ID NO: 15, including post-translational modifications of that sequence.

In another aspect, an anti-human collagen II antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human collagen II antibody comprising that sequence retains the ability to bind to human collagen II. In certain embodiments, a total of 1 to 10 amino acids have been substituted, inserted and/or deleted in SEQ ID NO: 10. In certain embodiments, the substitutions, insertions, or deletions occur in regions outside the HVRs (i.e., in the FRs). Optionally, the anti-human collagen II antibody comprises the VL sequence in SEQ ID NO: 10, including post-translational modifications of that sequence.

In another aspect, an anti-human collagen II antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 13. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human collagen II antibody comprising that sequence retains the ability to bind to human collagen II. In certain embodiments, a total of 1 to 10 amino acids have been substituted, inserted and/or deleted in SEQ ID NO: 13. In certain embodiments, the substitutions, insertions, or deletions occur in regions outside the HVRs (i.e., in the FRs). Optionally, the anti-human collagen II antibody comprises the VL sequence in SEQ ID NO: 13, including post-translational modifications of that sequence.

In another aspect, an anti-human collagen II antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 16. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human collagen II antibody comprising that sequence retains the ability to bind to human collagen II. In certain embodiments, a total of 1 to 10 amino acids have been substituted, inserted and/or deleted in SEQ ID NO: 16. In certain embodiments, the substitutions, insertions, or deletions occur in regions outside the HVRs (i.e., in the FRs). Optionally, the anti-human collagen II antibody comprises the VL sequence in SEQ ID NO: 16, including post-translational modifications of that sequence.

In another aspect, an anti-human collagen II antibody is provided, wherein the antibody comprises a VH as in any of the embodiments provided above, and a VL as in any of the embodiments provided above. In one embodiment, the antibody comprises the VH and VL sequences in SEQ ID NO: 09 and SEQ ID NO: 10, respectively, including post-translational modifications of those sequences.

In another aspect, an anti-human collagen II antibody is provided, wherein the antibody comprises a VH as in any of the embodiments provided above, and a VL as in any of the embodiments provided above. In one embodiment, the antibody comprises the VH and VL sequences in SEQ ID NO: 12 and SEQ ID NO: 13, respectively, including post-translational modifications of those sequences.

In another aspect, an anti-human collagen II antibody is provided, wherein the antibody comprises a VH as in any of the embodiments provided above, and a VL as in any of the embodiments provided above. In one embodiment, the antibody comprises the VH and VL sequences in SEQ ID NO: 15 and SEQ ID NO: 16, respectively, including post-translational modifications of those sequences.

In a further aspect, the invention provides an antibody that binds to the same epitope as an anti-human collagen II antibody provided herein.

In a further aspect of the invention, an anti-human collagen II antibody according to any of the above embodiments is a monoclonal antibody, including a chimeric, humanized or human antibody. In one embodiment, an anti-human collagen II antibody is an antibody fragment, e.g., a Fv, Fab, Fab', scFv, diabody, or F(ab')$_2$ fragment.

In a further aspect of the invention, an anti-human collagen II antibody according to any of the above embodiments is a monoclonal antibody scFv fragment or Fab. In one embodiment the scFv fragment has an amino acid sequence of SEQ ID NO: 11. In one embodiment the scFv fragment has an amino acid sequence of SEQ ID NO: 14. In one embodiment the scFv fragment has an amino acid sequence of SEQ ID NO: 17.

IV. Production

The multispecific binder/fusion protein as disclosed herein is produced by recombinant means. Thus, one aspect as reported herein is a nucleic acid encoding the multispecific binder as reported herein and a further aspect is a cell comprising the nucleic acid encoding a multispecific binder as reported herein. Methods for recombinant production are widely known in the state of the art and comprise protein expression in prokaryotic and eukaryotic cells with subsequent isolation of the multispecific binder and usually purification to a pharmaceutically acceptable purity. For the expression of the multispecific binder as aforementioned in a host cell, nucleic acids encoding the respective chains are inserted into expression vectors by standard methods. Expression is performed in appropriate prokaryotic or eukaryotic host cells like CHO cells, NSO cells, SP2/0 cells, HEK293 cells, COS cells, PER.C6 cells, yeast, or E. coli cells, and the multispecific binder is recovered from the cells (cultivation supernatant or cells after lysis). General methods for recombinant production of antibodies are well-known in the state of the art and described, for example, in the review articles of Makrides, S. C., Protein Expr. Purif. 17 (1999) 183-202, Geisse, S., et al., Protein Expr. Purif. 8 (1996) 271-282, Kaufman, R. J., Mol. Biotechnol. 16 (2000) 151-160, and Werner, R. G., Drug Res. 48 (1998) 870-880.

Antibodies may be produced using recombinant methods and formulations, e.g., as described in U.S. Pat. No. 4,816,567.

In one embodiment, isolated nucleic acid(s) encoding a multispecific binder as described herein is(are) provided. Such nucleic acid may encode an amino acid sequence comprising the VL and/or an amino acid sequence comprising the VH of the multispecific binder. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the multispecific binder and an amino acid sequence comprising the VH of the multispecific binder, or (2) a first vector comprising a nucleic acid that encodes an amino acid sequence comprising the VL of the multispecific binder and a second vector comprising a nucleic acid that encodes an amino acid sequence comprising the VH of the multispecific binder. In one embodiment, the host cell is eukaryotic, e.g. a Chinese Hamster Ovary (CHO) cell or lymphoid cell (e.g., Y0, NS0, Sp20 cell). In one embodiment, a method of making a multispecific binder as reported herein is provided, wherein the method comprises culturing a host cell comprising a nucleic acid encoding the multispecific binder, as provided above, under conditions suitable for expression of the multispecific binder, and optionally recovering the multispecific binder from the host cell (or host cell culture medium).

Accordingly one aspect as reported herein is a method for the preparation of a multispecific binder as reported herein, comprising the steps of a) transforming a host cell with vectors comprising nucleic acid molecules encoding the multispecific binder, b) culturing the host cell under conditions that allow synthesis of the multi specific binder, and c) recovering the multispecific binder from the culture.

In one embodiment the recovering step under c) includes the use of a light chain constant domain specific capture reagent (which e.g. specific for the kappa or the lambda constant light chain, depending on whether a kappa or a lambda light chain is contained in the bi specific antibody). In one embodiment this light chain specific capture reagent is used in in a bind-and-elute-mode. Examples of such light chain constant domain specific capture reagents are e.g. KappaSelect™ and LambdaFabSelect™ (available from GE Healthcare/BAC), which are based on a highly rigid agarose base matrix that allows high flow rates and low back pressure at large scale. These materials contain a ligand that binds to the constant region of the kappa or the lambda light chain, respectively (i.e. fragments lacking the constant region of the light chain will not bind). Both are therefore capable of binding other target molecules containing the constant region of the light chain, for example, IgG, IgA and IgM. The ligands are attached to the matrix via a long hydrophilic spacer arm to make them easily available for binding to the target molecule.

They are based on a single-chain antibody fragment that is screened for either human Ig kappa or lambda.

The multispecific binders are suitably separated from the culture medium by conventional immunoglobulin purification procedures such as, for example, affinity chromatography (protein A-Sepharose, or KappaSelect™, LambdaFabSelect™), hydroxylapatite chromatography, gel electrophoresis, or dialysis.

DNA and RNA encoding monoclonal antibodies is readily isolated and sequenced using conventional procedures. B-cells or hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Purification of multispecific binder is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art (see e.g. Ausubel, F., et al., ed. Current Protocols in Molecular Biology, Greene Publishing and Wiley Interscience, New York (1987)). Different methods are well established and widespread used for protein purification, such as affinity chromatography (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

Suitable host cells for cloning or expression of multispecific binder-encoding vectors include prokaryotic or eukaryotic cells described herein. For example, multispecific binder may be produced in bacteria, in particular when glycosylation is not needed. For expression of polypeptides in bacteria, see, e.g., U.S. Pat. Nos. 5,648,237, 5,789,199, and 5,840,523 (see also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli.*). After expression, the multispecific binder may be isolated from the bacterial cell paste in a soluble fraction and can be further purified.

In addition to prokaryotes, eukaryotic microbes such as filamentous fungi or yeast are suitable cloning or expression hosts for multispecific binder-encoding vectors, including fungi and yeast strains whose glycosylation pathways have been "humanized", resulting in the production of a multispecific binder with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated multispecific binder are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (BELA); canine kidney cells (MDCK); buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

V. Pharmaceutical Formulation

The multispecific binder/fusion proteins as disclosed herein may have a valuable efficacy/safety profile and may provide benefits for a patient in the need of the respective therapy.

In one aspect, a multispecific binder as reported herein for use as a medicament is provided.

In a further aspect, the invention provides for the use of a multi specific binder in the manufacture or preparation of a medicament. An "individual" according to any embodiments may be a human.

In a further aspect, the invention provides pharmaceutical formulations comprising any of the multispecific binder provided herein, e.g., for use in any of the herein outlined therapeutic methods. In one embodiment, a pharmaceutical formulation comprises any of the multi specific binder provided herein and a pharmaceutically acceptable carrier. In another embodiment, a pharmaceutical formulation comprises any of the multispecific binder provided herein and at least one additional therapeutic agent.

One aspect as reported herein is a pharmaceutical formulation comprising a multispecific binder as reported herein.

Pharmaceutical formulations of a multispecific binder as described herein are prepared by mixing such multispecific binder having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol, and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO 2006/044908, the latter formulations including a hi stidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Another aspect as reported herein is the use of a multispecific binder as reported herein for the manufacture of a pharmaceutical formulation. A further aspect as reported herein is a method for the manufacture of a pharmaceutical formulation comprising a multispecific binder as reported herein. In another aspect, a formulation is provided, e.g. a pharmaceutical formulation, containing a multispecific binder as reported herein, formulated together with a pharmaceutical carrier.

Many possible modes of delivery can be used, including, but not limited to intraocular application or topical application. In one embodiment the application is intraocular and includes, but it's not limited to, subconjunctval injection, intracanieral injection, injection into the anterior chamber via the termporai limbus, intrastromal injection, intracorneal injection, subretinal injection, aqueous humor injection, subtenon injection or sustained delivery device, intravitreal injection (e.g., front, mid or back vitreal injection). In one embodiment the application is topical and includes, but it's not limited to eye drops to the cornea.

In one embodiment the multispecific binder or pharmaceutical formulation as reported herein is administered via intravitreal application, e.g. via intravitreal injection. This can be performed in accordance with standard procedures known in the art (see, e.g., Ritter et al., J. Clin. Invest. 116 (2006) 3266-3276, Russelakis-Carneiro et al., Neuropathol. Appl. Neurobiol. 25 (1999) 196-206, and Wray et al., Arch. Neurol. 33 (1976) 183-185).

In some embodiments, therapeutic kits are provided that contain one or more doses of a multispecific binder present in a pharmaceutical formulation described herein, a suitable device for intravitreal injection of the pharmaceutical formulation, and an instruction detailing suitable subjects and protocols for carrying out the injection. In these embodiments, the formulations are typically administered to the subject in need of treatment via intravitreal injection. This can be performed in accordance with standard procedures known in the art (see, e.g., Ritter et al., J. Clin. Invest. 116 (2006) 3266-3276, Russelakis-Carneiro et al., Neuropathol. Appl. Neurobiol. 25 (1999) 196-206, and Wray et al., Arch. Neurol. 33 (1976) 183-185).

The formulations may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the formulations. In addition, prolonged absorption of the injectable pharmaceutical form may be brought about by the inclusion of agents, which delay absorption such as aluminum monostearate and gelatin.

Regardless of the route of administration selected, the multispecific binder as reported herein, which may be used in a suitable hydrated form, and/or the pharmaceutical formulations as reported herein, are formulated into pharmaceutically acceptable dosage forms by conventional methods known to those of skill in the art.

Actual dosage levels of the active ingredients in the pharmaceutical formulations as reported herein may be varied so as to obtain an amount of the active ingredient which is effective to achieve the desired therapeutic response for a particular patient, formulation, and mode of administration, without being toxic to the patient. The selected dosage level will depend upon a variety of pharmacokinetic factors including the activity of the particular formulations employed, the route of administration, the time of administration, the rate of excretion of the particular compound being employed, the duration of the treatment, other drugs, compounds and/or materials used in combination with the particular formulations employed, the age, sex, weight, condition, general health and prior medical history of the patient being treated, and like factors well known in the medical arts.

The formulation must be sterile and fluid to the extent that the formulation is deliverable by syringe. In addition to water, the carrier preferably is an isotonic buffered saline solution.

Proper fluidity can be maintained, for example, by use of surfactants. In many cases, it is preferable to include isotonic agents, for example, sugars, polyalcohols such as mannitol or sorbitol, and sodium chloride in the formulation.

The formulation can comprise an ophthalmic depot formulation comprising an active agent for subconjunctival administration. The ophthalmic depot formulation comprises microparticles of essentially pure active agent, e.g., the multi specific binder as reported herein. The microparticles comprising the multispecific binder as reported herein can be embedded in a biocompatible pharmaceutically acceptable polymer or a lipid-encapsulating agent. The depot formulations may be adapted to release all of substantially all the active material over an extended period of time. The polymer or lipid matrix, if present, may be adapted to degrade sufficiently to be transported from the site of administration after release of all or substantially all of the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

Another aspect as reported herein is the multispecific binder as reported herein for use in the treatment of ocular vascular diseases.

Another aspect as reported herein is the pharmaceutical formulation as reported herein for use in the treatment of ocular vascular diseases.

Another aspect as reported herein is the use of a multispecific binder as reported herein for the manufacture of a medicament for the treatment of ocular vascular disease.

Another aspect as reported herein is method of treatment of patient suffering from ocular vascular diseases by administering a multi specific binder as reported herein to a patient in the need of such treatment.

VI. Therapeutic Methods

Any of the multispecific binder/fusion proteins disclosed herein may be used in therapeutic methods.

In certain embodiments, a multispecific binder for use in a method of treatment is provided. In one such embodiment, the method further comprises administering to the individual an effective amount of at least one additional therapeutic agent, e.g., as described below. An "individual" according to any of the above embodiments is in one preferred embodiment a human.

In certain embodiments, a multispecific binder for use in a method of treatment is provided. In one such embodiment, the method further comprises administering to the individual an effective amount of at least one additional therapeutic agent, e.g., as described below. An "individual" according to any of the embodiments is in one preferred embodiment a human.

Multispecific binder as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The multispecific binder need not be, but is optionally formulated with one or more agents currently used to prevent or treat the disorder in question. The effective amount of such other agents depends on the amount of multispecific binder present in the formulation, the type of disorder or treatment, and other factors discussed above. These are generally used in the same dosages and with administration routes as described herein, or in any dosage and by any route that is empirically/clinically determined to be appropriate.

For the prevention or treatment of disease, the appropriate dosage of a multispecific binder as reported herein (when used alone or in combination with one or more other additional therapeutic agents) will depend on the type of disease to be treated, the type of multispecific binder, the severity and course of the disease, whether the multispecific binder is administered for preventive or therapeutic purposes, previous therapy, the patient's clinical history and response to the multispecific binder, and the discretion of the attending physician. The multispecific binder is suitably administered to the patient at one time or over a series of treatments. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

VII. Articles of Manufacture

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a formulation, which is by itself or combined with another formulation effective for treating, preventing and/or diagnosing the condition and may have a sterile access port (for example the container may be an intravenous solution bag or a vial having a stopper pierceable by a hypodermic injection needle). At least one active agent in the formulation is a multi specific binder as reported herein. The label or package insert indicates that the formulation is used for treating the condition of choice. Moreover, the article of manufacture may comprise (a) a first container with a formulation contained therein, wherein the formulation comprises a multispecific binder as reported herein; and (b) a second container with a formulation contained therein, wherein the formulation comprises a further therapeutic agent. The article of manufacture in this embodiment as reported herein may further comprise a package insert indicating that the formulations can be used to treat a particular condition. Alternatively, or additionally, the article of manufacture may further comprise a second (or third) container comprising a pharmaceutically acceptable buffer, such as bacteriostatic water for injection (BWFI) or phosphate-buffered saline. It may further include other materials desirable from a commercial and user standpoint, including other buffers, diluents, filters, needles, and syringes.

VIII. Modifications

In a further aspect, a multispecific binder according to any of the above embodiments may incorporate any of the features, singly or in combination, as described in Sections 1-5 below:

1. Antibody Affinity

In certain embodiments, the multispecific binder provided herein has an equilibrium dissociation constant ($K_D$) of ≤100 nM (e.g. $10^{-7}$ M or less, e.g. from $10^{-7}$ M to $10^{-13}$) for any of its targets.

In one embodiment, $K_D$ is measured using a BIACORE® surface plasmon resonance assay. For example, an assay using a BIACORE®-2000 or a BIACORE®-3000 (GE Healthcare Inc., Piscataway, N.J.) is performed at 25° C. with immobilized antigen CM5 chips at ~10 response units (RU). In one embodiment, carboxymethylated dextran biosensor chips (CM5, GE Healthcare Inc.) are activated with N-ethyl-N'—(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/mL (~0.2 μM) before injection at a flow rate of 5 μL/minute to achieve approximately 10 response units (RU) of coupled protein. Following the injection of antigen, 1 M ethanolamine is injected to block non-reacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Chimeric and Humanized Binding Sites

In certain embodiments, a multispecific binder provided herein comprises an antibody binding site of a chimeric or humanized antibody.

Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); Osbourn, J. et al., Methods 36 (2005) 61-68; and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Human Antibody Binding Sites

In certain embodiments, a multispecific binder provided herein comprises an antibody binding site of a human antibody.

Human antibodies can be produced using various techniques known in the art. Human antibodies are described generally in van Dijk, M. A. and van de Winkel, J. G., Curr. Opin. Pharmacal. 5 (2001) 368-374 and Lonberg, N., Curr. Opin. Immunol. 20 (2008) 450-459.

Human antibodies maybe prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95). Human antibodies generated via human B-cell hybridoma technology are also described in Li, J.et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibody Binding Sites

Multispecific binder as reported herein may comprise an antibody binding site of an antibody isolated by screening combinatorial libraries for antibodies with the desired activity or activities.

For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455.Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Binder Variants

In certain embodiments, amino acid sequence variants of the multispecific binder provided herein are contemplated. For example, it may be desirable to improve the binding affinity and/or other biological properties of the multispecific binder. Amino acid sequence variants of a multispecific binder may be prepared by introducing appropriate modifications into the nucleotide sequence encoding the multispecific binder, or by peptide synthesis. Such modifications include, for example, deletions from, and/or insertions into and/or substitutions of residues within the amino acid sequences of the multispecific binder. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, multispecific binder variants having one or more amino acid substitutions are provided. Sites of interest for substitutional mutagenesis include the HVRs and FRs. Conservative substitutions are shown in the Table below under the heading of "preferred substitutions". More substantial changes are provided in the following Table under the heading of "exemplary substitutions", and as further described below in reference to amino acid side chain classes. Amino acid substitutions may be introduced into a multispecific binder of interest and the products screened for a desired activity, e.g., retained/improved antigen binding, decreased immunogenicity, or improved ADCC or CDC.

TABLE

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent multispecific binder (e.g. a humanized or human antibody). Generally, the resulting variant(s) selected for further study will have modifications (e.g., improvements) in certain biological properties (e.g., increased affinity, reduced immunogenicity) relative to the parent antibody multispecific binder and/or will have substantially retained certain biological properties of the parent antibody. An exemplary substitutional variant is an affinity matured multispecific binder, which may be conveniently generated, e.g., using phage display-based affinity maturation techniques such as those described herein. Briefly, one or more HVR residues are mutated and the variant multispecific binder displayed on phage and screened for a particular biological activity (e.g. binding affinity).

Alterations (e.g., substitutions) may be made in HVRs, e.g., to improve multispecific binder affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any multispecific binder variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the multispecific binder to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of a multispecific binder that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the multispecific binder with antigen is affected. Further substitutions may be introduced at the amino acid locations demonstrating functional sensitivity to the initial substitutions. Alternatively, or additionally, a crystal structure of an antigen-multispecific binder complex to identify contact points between the multispecific binder and antigen can be used. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a multispecific binder with an N-terminal methionyl residue. Other insertional variants of the multispecific binder molecule include the fusion to the N- or C-terminus of the multispecific binder to an enzyme (e.g. for ADEPT) or a polypeptide.

The following examples, sequences and figures are provided to aid the understanding of the present invention, the true scope of which is set forth in the appended claims. It is understood that modifications can be made in the procedures set forth without departing from the spirit of the invention.

MATERIALS AND METHODS

Recombinant DNA Techniques

Figure 1:
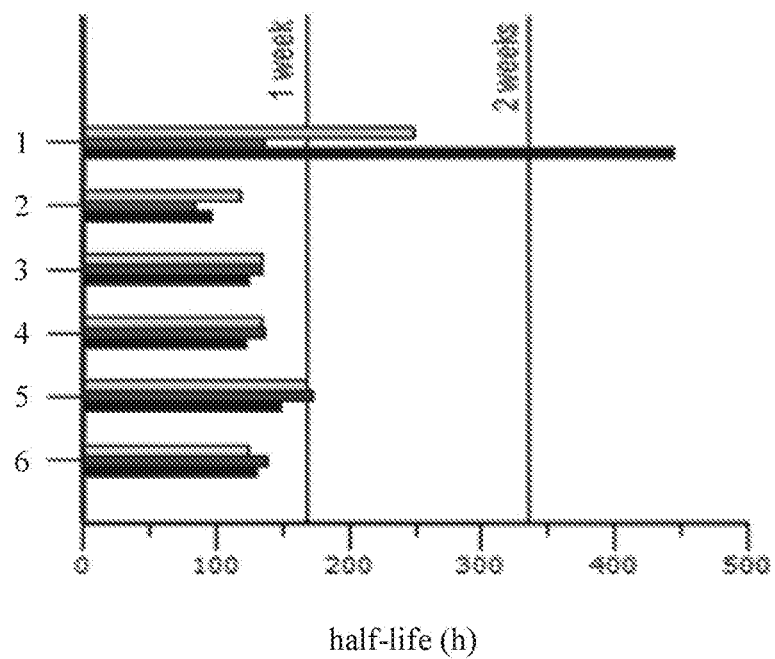
FIG. 1 Half-life of the different constructs in the different compartments of the eye; 1: FAB-PEG, 2: FAB-HBD, 3: FAB, 4: FAB-COLL-1, 5: FAB-COLL-II, 6: FAB-COLL-III; upper bar: vitreous, middle bar: retina, lower bar: choroid.
Figure 2:
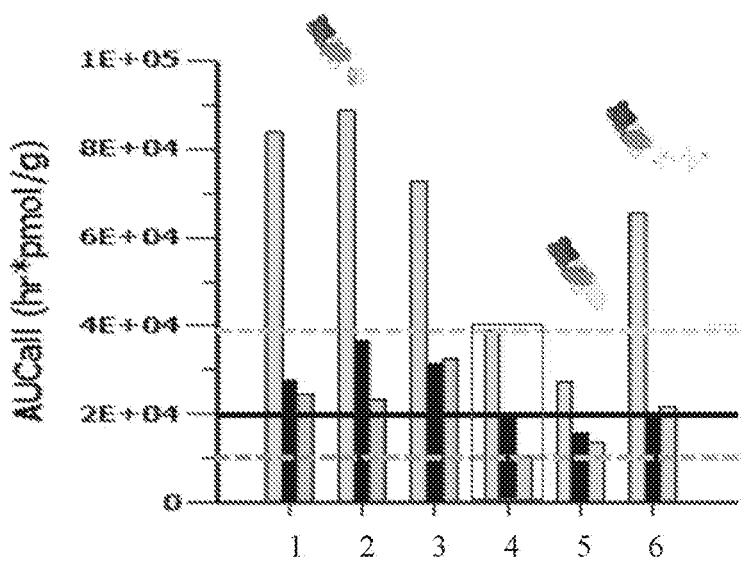
FIG. 2 Exposure of different compartments (tissues) of the eye to the different constructs; 1: FAB-COLL-I, 2: FAB-COLL-II, 3: FAB-COLL-III, 4: FAB, 5: FAB-HBD, 6: FAB-PEG; left bar: vitreous, middle bar: retina, right bar: choroid.

Standard methods were used to manipulate DNA as described in Sambrook, J. et al., Molecular Cloning: A laboratory manual; Cold Spring Harbor Laboratory Press, Cold Spring Harbor, N.Y. (1989). The molecular biological reagents were used according to the manufacturer's instructions.

Gene Synthesis

Desired gene segments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies expression plasmids for transient expression (e.g. in HEK293-F cells) based either on a cDNA organization with or without a CMV-Intron A promoter or on a genomic organization with a CMV promoter were used.

The transcription unit of the antibody gene was composed of the following elements:
  unique restriction site(s) at the 5' end,
  the immediate early enhancer and promoter from the human cytomegalovirus,
  in the case of the cDNA organization the Intron A sequence,
  a 5'-untranslated region of a human immunoglobulin gene,
  a nucleic acid encoding an immunoglobulin heavy chain signal sequence,
  a nucleic acid encoding the human antibody chain (wild-type or with domain exchange) either as cDNA or in genomic organization with the immunoglobulin exon-intron organization,
  a 3' non-translated region with a polyadenylation signal sequence, and
  unique restriction site(s) at the 3' end.

Beside the antibody expression cassette the plasmids contained:
  an origin of replication which allows replication of this plasmid in $E.\ coli$,
  a β-lactamase gene which confers ampicillin resistance in $E.\ coli$., and
  the dihydrofolate reductase gene from Mus musculus as a selectable marker in eukaryotic cells.

The nucleic acids encoding the antibody chains were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed $E.\ coli$ cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The bispecific antibodies were expressed by transient co-transfection of the respective expression plasmids in in HEK293-F cells growing in suspension as described below.

Example 1

Expression and Purification

Transient transfections in HEK293-F system

The fusion constructs were generated by transient transfection with the respective plasmids using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the respective expression plasmids and 293fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of approx. $1.5*10^6$ cells/mL with approx. 42 mL of a mixture of A) 20 mL Opti-MEM (Invitrogen) with 600 μg total plasmid DNA (1 μg/mL) encoding the heavy or modified heavy chain, respectively and the corresponding light chain in an equimolar ratio and B) 20 ml Opti-MEM with 1.2 mL 293 fectin or fectin (2 μL/mL). According to the glucose consumption glucose solution was added during the course of the fermentation. The supernatant containing the secreted antibody was harvested after 5-10 days and antibodies were either directly purified from the supernatant or the supernatant was frozen and stored.

Purification

The polypeptide-containing culture supernatants were filtered and purified by two chromatographic steps. The antibodies were captured by affinity chromatography using HiTrap KappaSelect (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the fusion polypeptide was recovered with 100 mM citrate buffer, pH 2.9, and immediately after elution neutralized to pH 6.0 with 1 M Tris-base, pH 9.0. Size exclusion chromatography on HiLoad 26/60 Superdex 75™ (GE Healthcare) was used as second purification step. The size exclusion chromatography was performed in 20 mM histidine buffer, 0.14 M NaCl, pH 6.0. The polypeptide containing solutions were concentrated with an Ultra free -CL centrifugal filter unit equipped with a Biomax-SK membrane (Millipore, Billerica, Mass.) and stored at −80° C.

The protein concentrations of the polypeptides were determined by measuring the optical density (OD) at 280 nm, using the molar extinction coefficient calculated on the basis of the amino acid sequence.

Purity and integrity of the polypeptides molecules were analyzed by CE-SDS using a LabChip GX II (PerkinElmer) with Protein Express Chip and HT Protein Express Reagents Kit.

Aggregate content was determined by high-performance SEC using a Biosuite High Resolution SEC, 250 Å, 5 μm analytical size-exclusion column (Waters GmbH) using 200 mM $K_2HPO_4/KH_2PO_4$, 250 mM KCl, pH 7.0 as running buffer.

The integrity of the amino acid backbone of reduced polypeptides was verified by Nano Electrospray QTOF mass spectrometry after removal of N-glycans by enzymatic treatment with a combination of neuraminidase, 0-glycanase and peptide-N-glycosidase F (Roche Applied Science).

Example 2

Binding to Human and Porcine Collagen II

Binding kinetics of anti-collagen antibodies to human Collage type II (Millipore CC052) and porcine Collagen type H (USBiological C7510-31) was investigated by surface plasmon resonance using a BIAcore T200 instrument (GE Healthcare). All experiments were performed at 25° C. using HBS-P (10 mM His, 140 mM NaCl, 0.05% Tween 20 pH 7.4) as running and dilution buffer. Collagen type II was immobilized on a Series S CM5 Sensor Chip (GE Healthcare) using standard amine coupling chemistry. Anti-Collagen antibodies were injected for 180 s with concentrations from 1.23 up to 900 nM (1:3 dilution series) onto the surface (association phase). The dissociation phase was monitored for 600 sec by washing with running buffer. The surface was regenerated by injecting 0.85% H3PO4 for 60 sec. Bulk refractive index differences were corrected by subtracting the response obtained from a mock surface. Blank injections were subtracted (double referencing). The derived curves were fitted to a 1:1 Langmuir binding model using the BIAevaluation software.

Example 3

Minipig Pharmacokinetic Study

Female minipigs, 7-8 kg each, were administered 1.25 nmol of each drug by IVT injection. The aimed initial concentration was 500 nM in the eye for each molecule. Vitreous, retina and choroid samples were collected at three termination time points 168, 336 and 672 hours after application.

Example 4

Pharmacokinetic Parameter Determination

Minipig serum, aqueous humor, vitreous humor and ocular tissue (retina, choroid, sclera, iris, lens, ciliary body) were analyzed with an ECLIA method using an ELECSYS instrument (Roche Diagnostics GmbH).

Briefly, test sample (calibrator, quality control or study sample), first detection antibody mAb<H-Fab(kappa)>M-1.7.10-IgG-Bi, second detection antibody mAb<Fab(CH1)>M-1.19.31-IgG-Ru, and SA-beads are added stepwise to a detection vessel and incubated for 9 minutes in each step. Finally, the SA-beads-bound complex is detected by a measuring cell, which numbers the counts of SA-beads in repeat. The counts are proportional to the analyte concentration in the test sample.

Bi=biotin, Ru=ruthenium label, SA=streptavidin

Prior to analysis, vitreous humor and ocular tissue samples were mechanically lysed in tissue extraction buffer (10 mM Tris, 137 mM NaCl, 1% Triton, 10% Glycerin) containing protease inhibitors using the Magana Lyser Homogenisator (Roche Diagnostics GmbH).

The assay calibration range for the three collagen binder conjugates FAB-COLL-I, -II, and -III was between 4.92 ng/mL and 3000 ng/mL (assay concentration).

Serum samples were diluted 1:10 to 1:20 to obtain valid results. Standard curve, quality control and sample dilutions were done in assay buffer incl. minipig serum resulting in 10% matrix concentration. Experimental serum samples below 49.2 ng/mL were annotated as "BLQ".

Aqueous humor, vitreous humor and ocular tissue samples were measured undiluted and diluted up to 1:50 to obtain valid results. Standard curve, quality control and sample dilutions were done in assay buffer without matrix. Experimental aqueous humor, vitreous humor and ocular tissue samples below 4.92 ng/mL were annotated as "BLQ".

Example 5

Diffusion Parameter Determination

The test solutions—vitreous fluid of minipigs—was stored at −80° C.

Dig-3-cme-eda-Cy5 was dissolved in DMF and adjusted to 1 mM Dig-Cy5 in 30% DMF/dilution buffer). A working stock was prepared as a 50 μM Dig-Cy5 solution in PBS/0.2% BSA/1.5% DMF. PBS was purchased at LONZA (#17-516F), pH 7.3-pH 7.5 and was supplemented with 0.2% BSA (fraction V). Measurements are done in 384-well glass bottom assay plates (MMI, #60200).

One sample was thawed on ice. The fluid is highly viscous and transparent. The sample was cautiously pipetted up and down ten times with a cropped 1000 μL tip. It does foam mildly. Aliquots of 100 μl (using a cropped 200 μl tip) are frozen on dry ice and stored at −80° C.

The other samples were thawed and liquefied alike. The bulk amount of all three samples is pooled, aliquoted and stored at −80° C. with sample name "all". Some original aliquots are stored as reference sample.

FCS measurements were performed with a ConfoCor2 FCS unit connected to an Axiovert 100M equipped with a C-Apochromat 40× N. A. 1.2 water immersion lens (Carl Zeiss, Jena, Germany). At this instrument Cy5 was excited with a 633 helium-neon laser. The red fluorescence emitted by Cy5 was detected with an LP 650 long pass filter. Measurements were performed typically with acquisition settings of 10 times for 10 seconds. The fluorescence fluctuations were auto-correlated with appropriate fitting formalisms. Data analysis allows determining the brightness, behavior and diffusion time of fluorescent particles in homogenous solution.

What is claimed is:

1. A method of treating an ocular vascular disease in an individual, the method comprising administering to the individual a multispecific binder comprising:
   (a) an anti-human collagen II antibody, or an antibody fragment thereof, comprising six CDRs determined according to Kabat from SEQ ID NO: 09 and SEQ ID NO: 10; and
   (b) an antibody, or an antibody fragment thereof, binding to a therapeutic ocular target wherein the therapeutic ocular target is selected from the group consisting of ANG2, VEGF, PDGF-B, and IL-1β.

2. The method of claim 1, wherein the anti-human collagen II antibody, or the antibody fragment thereof, comprises a heavy chain variable domain with the amino acid sequence of SEQ ID NO: 09 and a light chain variable domain with the amino acid sequence of SEQ ID NO: 10.

3. The method of claim 1, wherein the anti-human collagen II antibody, or the antibody fragment thereof, comprises a scFv.

4. A method of treating an ocular vascular disease in an individual, the method comprising administering to the individual a fusion protein comprising:
   (a) a Fab specifically binding to a therapeutic ocular target wherein the therapeutic ocular target is selected from the group consisting of ANG2, VEGF, PDGF-B, and IL-1β; and
   (b) a scFv specifically binding to collagen II,
      wherein the scFv specifically binding to collagen II comprises six CDRs determined according to Kabat from SEQ ID NO: 09 and SEQ ID NO: 10,
      wherein the Fab is conjugated by a peptide bond at one of its C-termini to the N-terminus of a peptidic linker and the scFv is conjugated by a peptide bond at its N-terminus to the C-terminus of the peptidic linker.

5. The method of claim 3, wherein the scFv comprises a peptidic linker.

6. The method of claim 2, wherein the anti-human collagen II antibody, or the fragment thereof, comprises the amino acid sequence of SEQ ID NO: 11.

7. The method of claim 4, wherein the scFv specifically binding to collagen II comprises the amino acid sequence of SEQ ID NO: 11.

* * * * *

UNITED STATES PATENT AND TRADEMARK OFFICE
CERTIFICATE OF CORRECTION

| | |
|---|---|
| PATENT NO. | : 11,673,942 B2 |
| APPLICATION NO. | : 17/066215 |
| DATED | : June 13, 2023 |
| INVENTOR(S) | : Michael Huelsmann et al. |

It is certified that error appears in the above-identified patent and that said Letters Patent is hereby corrected as shown below:

On the Title Page

In Column 1, under Related U.S. Application Data, Line 1, delete "(60)" and insert -- (63) --, therefor.

In Column 2, item (57), under Abstract, Line 4, delete "eye a multispecific binder provides" and insert -- eye taught herein results in a multispecific binder providing --, therefor.

In the Claims

In Column 77, Claim 1, Line 9, delete "ocular target wherein" and insert -- ocular target, wherein --, therefor.

In Column 78, Claim 4, Lines 1-2, delete "ocular target wherein" and insert -- ocular target, wherein --, therefor.

Signed and Sealed this
Thirtieth Day of April, 2024

Katherine Kelly Vidal
*Director of the United States Patent and Trademark Office*

SEQUENCE LISTING

```
<160> NUMBER OF SEQ ID NOS: 24

<210> SEQ ID NO 1
<211> LENGTH: 228
<212> TYPE: PRT
<213> ORGANISM: Artificial Sequence
<220> FEATURE:
<223> OTHER INFORMATION: anti-digoxigenin Fab HC

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 2
<211> LENGTH: 214
<212> TYPE: PRT
<213> ORGANISM: Artificial Sequence
<220> FEATURE:
<223> OTHER INFORMATION: anti-digoxigenin Fab LC

<400> SEQUENCE: 2

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 293
<212> TYPE: PRT
<213> ORGANISM: Artificial Sequence
<220> FEATURE:
<223> OTHER INFORMATION: anti-digoxigenin Fab + HBD HC

<400> SEQUENCE: 3

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Gly Gly Gly Ser Gly Gly Gly Ser Ala Arg
225                 230                 235                 240

Gln Glu Asn Pro Cys Gly Pro Cys Ser Glu Arg Arg Lys His Leu Phe
            245                 250                 255

Val Gln Asp Pro Gln Thr Cys Lys Cys Ser Cys Lys Asn Thr Asp Ser
            260                 265                 270

Arg Cys Lys Ala Arg Gln Leu Glu Leu Asn Glu Arg Thr Cys Arg Cys
            275                 280                 285

Asp Lys Pro Arg Arg
            290

<210> SEQ ID NO 4
<211> LENGTH: 488
<212> TYPE: PRT
<213> ORGANISM: Artificial Sequence
<220> FEATURE:
<223> OTHER INFORMATION: anti-digoxigenin Fab + anti-collagen II scFV I
      HC

<400> SEQUENCE: 4

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
```

Pro Lys Ser Cys Gly Gly Gly Ser Gly Gly Gly Ser Glu Ile
225                 230                 235                 240

Val Leu Thr Gln Ser Pro Ala Thr Leu Ser Leu Ser Pro Gly Glu Arg
            245                 250                 255

Ala Thr Leu Ser Cys Arg Ala Ser Gln Ser Val Arg Asp Phe Leu Ala
                260                 265                 270

Trp Tyr Gln Gln Lys Pro Gly Gln Ala Pro Arg Leu Leu Ile Tyr Gly
            275                 280                 285

Ala Ser Asn Arg Ala Thr Gly Ile Pro Ala Arg Phe Ser Gly Ser Gly
        290                 295                 300

Ser Gly Thr Asp Phe Thr Leu Thr Ile Ser Ser Leu Glu Pro Glu Asp
305                 310                 315                 320

Phe Ala Val Tyr Tyr Cys Gln Gln Arg Gly Ser Ala Pro Leu Thr Phe
                325                 330                 335

Gly Gln Gly Thr Lys Val Glu Ile Lys Gly Gly Gly Ser Gly Gly
            340                 345                 350

Gly Gly Ser Gly Gly Gly Ser Gly Gly Gly Ser Gln Val Gln
        355                 360                 365

Leu Val Gln Ser Gly Ala Glu Val Lys Lys Pro Gly Ser Ser Val Lys
370                 375                 380

Val Ser Cys Lys Ala Ser Gly Gly Thr Phe Ser Ser Tyr Ala Ile Ser
385                 390                 395                 400

Trp Val Arg Gln Ala Pro Gly Gln Gly Leu Glu Trp Met Gly Gly Ile
                405                 410                 415

Ile Pro Ile Phe Gly Thr Ala Asn Tyr Ala Gln Lys Phe Gln Gly Arg
            420                 425                 430

Val Thr Ile Thr Ala Asp Glu Ser Thr Ser Thr Ala Tyr Met Glu Leu
        435                 440                 445

Ser Ser Leu Arg Ser Glu Asp Thr Ala Val Tyr Tyr Cys Ala Arg Asp
    450                 455                 460

Pro Asn Gly Asn Ile Val Leu Ser Glu Tyr Phe Asp Tyr Trp Gly Gln
465                 470                 475                 480

Gly Thr Leu Val Thr Val Ser Ser
                485

<210> SEQ ID NO 5
<211> LENGTH: 484
<212> TYPE: PRT
<213> ORGANISM: Artificial Sequence
<220> FEATURE:
<223> OTHER INFORMATION: anti-digoxigenin Fab + anti-collagen II scFV II
    HC

<400> SEQUENCE: 5

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130             135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Gly Gly Gly Ser Gly Gly Gly Ser Glu Ile
225                 230                 235                 240

Val Leu Thr Gln Ser Pro Ala Thr Leu Ser Leu Ser Pro Gly Glu Arg
                245                 250                 255

Ala Thr Leu Ser Cys Arg Ala Ser Gln Ser Val Asp Asp Trp Leu Ala
            260                 265                 270

Trp Tyr Gln Gln Lys Pro Gly Gln Ala Pro Arg Leu Leu Ile Tyr Asp
        275                 280                 285

Ala Ser Asn Arg Ala Thr Gly Ile Pro Ala Arg Phe Ser Gly Ser Gly
290                 295                 300

Ser Gly Thr Asp Phe Thr Leu Thr Ile Ser Ser Leu Glu Pro Glu Asp
305                 310                 315                 320

Phe Ala Val Tyr Tyr Cys Gln Gln Gly Asp Thr Ala Pro Ile Thr Phe
                325                 330                 335

Gly Gln Gly Thr Lys Val Glu Ile Lys Gly Gly Gly Ser Gly Gly
            340                 345                 350

Gly Gly Ser Gly Gly Gly Ser Gly Gly Gly Gly Ser Gln Val Gln
        355                 360                 365

Leu Val Gln Ser Gly Ala Glu Val Lys Lys Pro Gly Ser Ser Val Lys
        370                 375                 380

Val Ser Cys Lys Ala Ser Gly Gly Thr Phe Ser Ser Tyr Ala Ile Ser
385                 390                 395                 400

Trp Val Arg Gln Ala Pro Gly Gln Gly Leu Glu Trp Met Gly Gly Ile
                405                 410                 415

Ile Pro Ile Phe Gly Thr Ala Asn Tyr Ala Gln Lys Phe Gln Gly Arg
            420                 425                 430

Val Thr Ile Thr Ala Asp Glu Ser Thr Ser Thr Ala Tyr Met Glu Leu
        435                 440                 445

Ser Ser Leu Arg Ser Glu Asp Thr Ala Val Tyr Tyr Cys Ala Arg Asn
450                 455                 460

Ile Val Gly Asp Tyr Leu Leu Asp Tyr Trp Gly Gln Gly Thr Leu Val
465                 470                 475                 480

Thr Val Ser Ser

<210> SEQ ID NO 6
```

<211> LENGTH: 482
<212> TYPE: PRT
<213> ORGANISM: Artificial Sequence
<220> FEATURE:
<223> OTHER INFORMATION: anti-digoxigenin Fab + anti-collagen II scFV III HC

<400> SEQUENCE: 6

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Gly Gly Gly Ser Glu Ile
225                 230                 235                 240

Val Leu Thr Gln Ser Pro Ala Thr Leu Ser Leu Ser Pro Gly Glu Arg
                245                 250                 255

Ala Thr Leu Ser Cys Arg Ala Ser Gln Ser Val Ala Asp Trp Leu Ala
            260                 265                 270

Trp Tyr Gln Gln Lys Pro Gly Gln Ala Pro Arg Leu Leu Ile Tyr Asp
        275                 280                 285

Ala Ser Asn Arg Ala Thr Gly Ile Pro Ala Arg Phe Ser Gly Ser Gly
    290                 295                 300

Ser Gly Thr Asp Phe Thr Leu Thr Ile Ser Ser Leu Glu Pro Glu Asp
305                 310                 315                 320

Phe Ala Val Tyr Tyr Cys Gln Gln Tyr Asp Gly Trp Pro Ile Thr Phe
                325                 330                 335

Gly Gln Gly Thr Lys Val Glu Ile Lys Gly Gly Gly Ser Gly Gly
            340                 345                 350

Gly Gly Ser Gly Gly Gly Gly Ser Gly Gly Gly Gly Ser Gln Val Gln
        355                 360                 365

Leu Val Gln Ser Gly Ala Glu Val Lys Lys Pro Gly Ser Ser Val Lys
```

```
                    370                 375                 380
Val Ser Cys Lys Ala Ser Gly Gly Thr Phe Ser Ser Tyr Ala Ile Ser
385                 390                 395                 400

Trp Val Arg Gln Ala Pro Gly Gln Gly Leu Glu Trp Met Gly Gly Ile
                405                 410                 415

Ile Pro Ile Phe Gly Thr Ala Asn Tyr Ala Gln Lys Phe Gln Gly Arg
                420                 425                 430

Val Thr Ile Thr Ala Asp Glu Ser Thr Ser Thr Ala Tyr Met Glu Leu
                435                 440                 445

Ser Ser Leu Arg Ser Glu Asp Thr Ala Val Tyr Tyr Cys Ala Arg His
                450                 455                 460

Leu Tyr Tyr Met Leu Asp Tyr Trp Gly Gln Gly Thr Leu Val Thr Val
465                 470                 475                 480

Ser Ser
```

<210> SEQ ID NO 7
<211> LENGTH: 10
<212> TYPE: PRT
<213> ORGANISM: Artificial Sequence
<220> FEATURE:
<223> OTHER INFORMATION: peptidic linker

<400> SEQUENCE: 7

```
Gly Gly Gly Gly Ser Gly Gly Gly Gly Ser
1               5                   10
```

<210> SEQ ID NO 8
<211> LENGTH: 20
<212> TYPE: PRT
<213> ORGANISM: Artificial Sequence
<220> FEATURE:
<223> OTHER INFORMATION: peptidic linker

<400> SEQUENCE: 8

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 9
<211> LENGTH: 123
<212> TYPE: PRT
<213> ORGANISM: Artificial Sequence
<220> FEATURE:
<223> OTHER INFORMATION: anti-collagen II scFV I VH

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Asp Pro Asn Gly Asn Ile Val Leu Ser Glu Tyr Phe Asp Tyr
            100                 105                 110

Trp Gly Gln Gly Thr Leu Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: anti-collagen II scFV I VL

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asp Phe
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Ser Ala Pro Leu
                85                  90                  95

Thr Phe Gly Gln Gly Thr Lys Val Glu Ile Lys
            100                 105

<210> SEQ ID NO 11
<211> LENGTH: 250
<212> TYPE: PRT
<213> ORGANISM: Artificial Sequence
<220> FEATURE:
<223> OTHER INFORMATION: anti-collagen II scFV I scFv

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asp Phe
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Ser Ala Pro Leu
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ser Ser
    130                 135                 140

Val Lys Val Ser Cys Lys Ala Ser Gly Gly Thr Phe Ser Ser Tyr Ala
145                 150                 155                 160

Ile Ser Trp Val Arg Gln Ala Pro Gly Gln Gly Leu Glu Trp Met Gly
                165                 170                 175

```
Gly Ile Ile Pro Ile Phe Gly Thr Ala Asn Tyr Ala Gln Lys Phe Gln
            180                 185                 190

Gly Arg Val Thr Ile Thr Ala Asp Glu Ser Thr Ser Thr Ala Tyr Met
            195                 200                 205

Glu Leu Ser Ser Leu Arg Ser Glu Asp Thr Ala Val Tyr Tyr Cys Ala
210                 215                 220

Arg Asp Pro Asn Gly Asn Ile Val Leu Ser Glu Tyr Phe Asp Tyr Trp
225                 230                 235                 240

Gly Gln Gly Thr Leu Val Thr Val Ser Ser
                245                 250

<210> SEQ ID NO 12
<211> LENGTH: 119
<212> TYPE: PRT
<213> ORGANISM: Artificial Sequence
<220> FEATURE:
<223> OTHER INFORMATION: anti-collagen II scFV II VH

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Ile Val Gly Asp Tyr Leu Leu Asp Tyr Trp Gly Gln Gly
            100                 105                 110

Thr Leu Val Thr Val Ser Ser
        115

<210> SEQ ID NO 13
<211> LENGTH: 107
<212> TYPE: PRT
<213> ORGANISM: Artificial Sequence
<220> FEATURE:
<223> OTHER INFORMATION: anti-collagen II scFV II VL

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Trp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Asp Thr Ala Pro Ile
                85                  90                  95

Thr Phe Gly Gln Gly Thr Lys Val Glu Ile Lys
```

<210> SEQ ID NO 14
<211> LENGTH: 246
<212> TYPE: PRT
<213> ORGANISM: Artificial Sequence
<220> FEATURE:
<223> OTHER INFORMATION: anti-collagen II scFV II scFv

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Trp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Asp Thr Ala Pro Ile
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ser Ser
    130                 135                 140

Val Lys Val Ser Cys Lys Ala Ser Gly Gly Thr Phe Ser Ser Tyr Ala
145                 150                 155                 160

Ile Ser Trp Val Arg Gln Ala Pro Gly Gln Gly Leu Glu Trp Met Gly
                165                 170                 175

Gly Ile Ile Pro Ile Phe Gly Thr Ala Asn Tyr Ala Gln Lys Phe Gln
            180                 185                 190

Gly Arg Val Thr Ile Thr Ala Asp Glu Ser Thr Ser Thr Ala Tyr Met
        195                 200                 205

Glu Leu Ser Ser Leu Arg Ser Glu Asp Thr Ala Val Tyr Tyr Cys Ala
    210                 215                 220

Arg Asn Ile Val Gly Asp Tyr Leu Leu Asp Tyr Trp Gly Gln Gly Thr
225                 230                 235                 240

Leu Val Thr Val Ser Ser
                245

<210> SEQ ID NO 15
<211> LENGTH: 115
<212> TYPE: PRT
<213> ORGANISM: Artificial Sequence
<220> FEATURE:
<223> OTHER INFORMATION: anti-collagen II scFV III VH

<400> SEQUENCE: 15

Gln Leu Val Gln Ser Gly Ala Glu Val Lys Lys Pro Gly Ser Ser Val
1               5                   10                  15

Lys Val Ser Cys Lys Ala Ser Gly Gly Thr Phe Ser Ser Tyr Ala Ile
            20                  25                  30

Ser Trp Val Arg Gln Ala Pro Gly Gln Gly Leu Glu Trp Met Gly Gly
        35                  40                  45

Ile Ile Pro Ile Phe Gly Thr Ala Asn Tyr Ala Gln Lys Phe Gln Gly
    50                  55                  60

Arg Val Thr Ile Thr Ala Asp Glu Ser Thr Ser Thr Ala Tyr Met Glu
 65                 70                  75                  80

Leu Ser Ser Leu Arg Ser Glu Asp Thr Ala Val Tyr Tyr Cys Ala Arg
                 85                  90                  95

His Leu Tyr Tyr Met Leu Asp Tyr Trp Gly Gln Gly Thr Leu Val Thr
                100                 105                 110

Val Ser Ser
        115

<210> SEQ ID NO 16
<211> LENGTH: 107
<212> TYPE: PRT
<213> ORGANISM: Artificial Sequence
<220> FEATURE:
<223> OTHER INFORMATION: anti-collagen II scFV III VL

<400> SEQUENCE: 16

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ala Asp Trp
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Asp Gly Trp Pro Ile
                 85                  90                  95

Thr Phe Gly Gln Gly Thr Lys Val Glu Ile Lys
                100                 105

<210> SEQ ID NO 17
<211> LENGTH: 244
<212> TYPE: PRT
<213> ORGANISM: Artificial Sequence
<220> FEATURE:
<223> OTHER INFORMATION: anti-collagen II scFV III scFv

<400> SEQUENCE: 17

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ala Asp Trp
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Asp Gly Trp Pro Ile
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Gly Ser Gly Gly Gly Gly Ser Gln
             115                 120                 125

Val Gln Leu Val Gln Ser Gly Ala Glu Val Lys Lys Pro Gly Ser Ser
            130                 135                 140

Val Lys Val Ser Cys Lys Ala Ser Gly Gly Thr Phe Ser Ser Tyr Ala
145                 150                 155                 160

Ile Ser Trp Val Arg Gln Ala Pro Gly Gln Gly Leu Glu Trp Met Gly
                165                 170                 175

Gly Ile Ile Pro Ile Phe Gly Thr Ala Asn Tyr Ala Gln Lys Phe Gln
            180                 185                 190

Gly Arg Val Thr Ile Thr Ala Asp Glu Ser Thr Ser Thr Ala Tyr Met
                195                 200                 205

Glu Leu Ser Ser Leu Arg Ser Glu Asp Thr Ala Val Tyr Tyr Cys Ala
210                 215                 220

Arg His Leu Tyr Tyr Met Leu Asp Tyr Trp Gly Gln Gly Thr Leu Val
225                 230                 235                 240

Thr Val Ser Ser

<210> SEQ ID NO 18
<211> LENGTH: 1418
<212> TYPE: PRT
<213> ORGANISM: Homo sapiens

<400> SEQUENCE: 18

Met Ile Arg Leu Gly Ala Pro Gln Thr Leu Val Leu Leu Thr Leu Leu
1               5                   10                  15

Val Ala Ala Val Leu Arg Cys Gln Gly Gln Asp Val Arg Gln Pro Gly
                20                  25                  30

Pro Lys Gly Gln Lys Gly Glu Pro Gly Asp Ile Lys Asp Ile Val Gly
            35                  40                  45

Pro Lys Gly Pro Pro Gly Pro Gln Gly Pro Ala Gly Glu Gln Gly Pro
50                  55                  60

Arg Gly Asp Arg Gly Asp Lys Gly Glu Lys Gly Ala Pro Gly Pro Arg
65                  70                  75                  80

Gly Arg Asp Gly Glu Pro Gly Thr Pro Gly Asn Pro Gly Pro Pro Gly
                85                  90                  95

Pro Pro Gly Pro Pro Gly Pro Pro Gly Leu Gly Gly Asn Phe Ala Ala
            100                 105                 110

Gln Met Ala Gly Gly Phe Asp Glu Lys Ala Gly Gly Ala Gln Leu Gly
        115                 120                 125

Val Met Gln Gly Pro Met Gly Pro Met Gly Pro Arg Gly Pro Pro Gly
130                 135                 140

Pro Ala Gly Ala Pro Gly Pro Gln Gly Phe Gln Gly Asn Pro Gly Glu
145                 150                 155                 160

Pro Gly Glu Pro Gly Val Ser Gly Pro Met Gly Pro Arg Gly Pro Pro
                165                 170                 175

Gly Pro Pro Gly Lys Pro Gly Asp Asp Gly Glu Ala Gly Lys Pro Gly
            180                 185                 190

Lys Ala Gly Glu Arg Gly Pro Pro Gly Pro Gln Gly Ala Arg Gly Phe
        195                 200                 205

Pro Gly Thr Pro Gly Leu Pro Gly Val Lys Gly His Arg Gly Tyr Pro
210                 215                 220

Gly Leu Asp Gly Ala Lys Gly Glu Ala Gly Ala Pro Gly Val Lys Gly
225                 230                 235                 240

Glu Ser Gly Ser Pro Gly Glu Asn Gly Ser Pro Gly Pro Met Gly Pro
                245                 250                 255

```
Arg Gly Leu Pro Gly Glu Arg Gly Thr Gly Pro Ala Gly Ala Ala
            260                 265                 270

Gly Ala Arg Gly Asn Asp Gly Gln Pro Gly Pro Ala Gly Pro Pro Gly
        275                 280                 285

Pro Val Gly Pro Ala Gly Pro Gly Phe Pro Gly Ala Pro Gly Ala
    290                 295                 300

Lys Gly Glu Ala Gly Pro Thr Gly Ala Arg Gly Pro Glu Gly Ala Gln
305                 310                 315                 320

Gly Pro Arg Gly Glu Pro Gly Thr Pro Gly Ser Pro Gly Pro Ala Gly
                325                 330                 335

Ala Ser Gly Asn Pro Gly Thr Asp Gly Ile Pro Gly Ala Lys Gly Ser
                340                 345                 350

Ala Gly Ala Pro Gly Ile Ala Gly Ala Pro Gly Phe Pro Gly Pro Arg
                355                 360                 365

Gly Pro Pro Gly Pro Gln Gly Ala Thr Gly Pro Leu Gly Pro Lys Gly
            370                 375                 380

Gln Thr Gly Glu Pro Gly Ile Ala Gly Phe Lys Gly Glu Gln Gly Pro
385                 390                 395                 400

Lys Gly Glu Pro Gly Pro Ala Gly Pro Gln Gly Ala Pro Gly Pro Ala
                405                 410                 415

Gly Glu Glu Gly Lys Arg Gly Ala Arg Gly Glu Pro Gly Gly Val Gly
            420                 425                 430

Pro Ile Gly Pro Pro Gly Glu Arg Gly Ala Pro Gly Asn Arg Gly Phe
            435                 440                 445

Pro Gly Gln Asp Gly Leu Ala Gly Pro Lys Gly Ala Pro Gly Glu Arg
    450                 455                 460

Gly Pro Ser Gly Leu Ala Gly Pro Lys Gly Ala Asn Gly Asp Pro Gly
465                 470                 475                 480

Arg Pro Gly Glu Pro Gly Leu Pro Gly Ala Arg Gly Leu Thr Gly Arg
                485                 490                 495

Pro Gly Asp Ala Gly Pro Gln Gly Lys Val Gly Pro Ser Gly Ala Pro
                500                 505                 510

Gly Glu Asp Gly Arg Pro Gly Pro Pro Gly Pro Gln Gly Ala Arg Gly
            515                 520                 525

Gln Pro Gly Val Met Gly Phe Pro Gly Pro Lys Gly Ala Asn Gly Glu
    530                 535                 540

Pro Gly Lys Ala Gly Glu Lys Gly Leu Pro Gly Ala Pro Gly Leu Arg
545                 550                 555                 560

Gly Leu Pro Gly Lys Asp Gly Glu Thr Gly Ala Ala Gly Pro Pro Gly
                565                 570                 575

Pro Ala Gly Pro Ala Gly Glu Arg Gly Glu Gln Gly Ala Pro Gly Pro
            580                 585                 590

Ser Gly Phe Gln Gly Leu Pro Gly Pro Gly Pro Gly Glu Gly
            595                 600                 605

Gly Lys Pro Gly Asp Gln Gly Val Pro Gly Glu Ala Gly Ala Pro Gly
    610                 615                 620

Leu Val Gly Pro Arg Gly Glu Arg Gly Phe Pro Gly Glu Arg Gly Ser
625                 630                 635                 640

Pro Gly Ala Gln Gly Leu Gln Gly Pro Arg Gly Leu Pro Gly Thr Pro
                645                 650                 655

Gly Thr Asp Gly Pro Lys Gly Ala Ser Gly Pro Ala Gly Pro Pro Gly
            660                 665                 670
```

-continued

Ala Gln Gly Pro Pro Gly Leu Gln Gly Met Pro Gly Glu Arg Gly Ala
            675                 680                 685

Ala Gly Ile Ala Gly Pro Lys Gly Asp Arg Gly Asp Val Gly Glu Lys
        690                 695                 700

Gly Pro Glu Gly Ala Pro Gly Lys Asp Gly Gly Arg Gly Leu Thr Gly
705                 710                 715                 720

Pro Ile Gly Pro Pro Gly Pro Ala Gly Ala Asn Gly Glu Lys Gly Glu
                725                 730                 735

Val Gly Pro Pro Gly Pro Ala Gly Ser Ala Gly Ala Arg Gly Ala Pro
            740                 745                 750

Gly Glu Arg Gly Glu Thr Gly Pro Pro Gly Pro Ala Gly Phe Ala Gly
            755                 760                 765

Pro Pro Gly Ala Asp Gly Gln Pro Gly Ala Lys Gly Glu Gln Gly Glu
        770                 775                 780

Ala Gly Gln Lys Gly Asp Ala Gly Ala Pro Gly Pro Gln Gly Pro Ser
785                 790                 795                 800

Gly Ala Pro Gly Pro Gln Gly Pro Thr Gly Val Thr Gly Pro Lys Gly
                805                 810                 815

Ala Arg Gly Ala Gln Gly Pro Pro Gly Ala Thr Gly Phe Pro Gly Ala
            820                 825                 830

Ala Gly Arg Val Gly Pro Pro Gly Ser Asn Gly Asn Pro Gly Pro Pro
            835                 840                 845

Gly Pro Pro Gly Pro Ser Gly Lys Asp Gly Pro Lys Gly Ala Arg Gly
        850                 855                 860

Asp Ser Gly Pro Pro Gly Arg Ala Gly Glu Pro Gly Leu Gln Gly Pro
865                 870                 875                 880

Ala Gly Pro Pro Gly Glu Lys Gly Glu Pro Gly Asp Asp Gly Pro Ser
                885                 890                 895

Gly Ala Glu Gly Pro Pro Gly Pro Gln Gly Leu Ala Gly Gln Arg Gly
            900                 905                 910

Ile Val Gly Leu Pro Gly Gln Arg Gly Glu Arg Gly Phe Pro Gly Leu
            915                 920                 925

Pro Gly Pro Ser Gly Glu Pro Gly Lys Gln Gly Ala Pro Gly Ala Ser
        930                 935                 940

Gly Asp Arg Gly Pro Pro Gly Pro Val Gly Pro Pro Gly Leu Thr Gly
945                 950                 955                 960

Pro Ala Gly Glu Pro Gly Arg Glu Gly Ser Pro Gly Ala Asp Gly Pro
                965                 970                 975

Pro Gly Arg Asp Gly Ala Ala Gly Val Lys Gly Asp Arg Gly Glu Thr
            980                 985                 990

Gly Ala Val Gly Ala Pro Gly Ala Pro Gly Pro Pro Gly Ser Pro Gly
            995                 1000                1005

Pro Ala Gly Pro Thr Gly Lys Gln Gly Asp Arg Gly Glu Ala Gly
    1010                1015                1020

Ala Gln Gly Pro Met Gly Pro Ser Gly Pro Ala Gly Ala Arg Gly
    1025                1030                1035

Ile Gln Gly Pro Gln Gly Pro Arg Gly Asp Lys Gly Glu Ala Gly
    1040                1045                1050

Glu Pro Gly Glu Arg Gly Leu Lys Gly His Arg Gly Phe Thr Gly
    1055                1060                1065

Leu Gln Gly Leu Pro Gly Pro Pro Gly Pro Ser Gly Asp Gln Gly
    1070                1075                1080

Ala Ser Gly Pro Ala Gly Pro Ser Gly Pro Arg Gly Pro Pro Gly

```
                    1085                1090                1095

Pro  Val  Gly  Pro  Ser  Gly  Lys  Asp  Gly  Ala  Asn  Gly  Ile  Pro  Gly
     1100                1105                1110

Pro  Ile  Gly  Pro  Pro  Gly  Pro  Arg  Gly  Arg  Ser  Gly  Glu  Thr  Gly
     1115                1120                1125

Pro  Ala  Gly  Pro  Pro  Gly  Asn  Pro  Gly  Pro  Pro  Gly  Pro  Pro  Gly
     1130                1135                1140

Pro  Pro  Gly  Pro  Gly  Ile  Asp  Met  Ser  Ala  Phe  Ala  Gly  Leu  Gly
     1145                1150                1155

Pro  Arg  Glu  Lys  Gly  Pro  Asp  Pro  Leu  Gln  Tyr  Met  Arg  Ala  Asp
     1160                1165                1170

Gln  Ala  Ala  Gly  Gly  Leu  Arg  Gln  His  Asp  Ala  Glu  Val  Asp  Ala
     1175                1180                1185

Thr  Leu  Lys  Ser  Leu  Asn  Asn  Gln  Ile  Glu  Ser  Ile  Arg  Ser  Pro
     1190                1195                1200

Glu  Gly  Ser  Arg  Lys  Asn  Pro  Ala  Arg  Thr  Cys  Arg  Asp  Leu  Lys
     1205                1210                1215

Leu  Cys  His  Pro  Glu  Trp  Lys  Ser  Gly  Asp  Tyr  Trp  Ile  Asp  Pro
     1220                1225                1230

Asn  Gln  Gly  Cys  Thr  Leu  Asp  Ala  Met  Lys  Val  Phe  Cys  Asn  Met
     1235                1240                1245

Glu  Thr  Gly  Glu  Thr  Cys  Val  Tyr  Pro  Asn  Pro  Ala  Asn  Val  Pro
     1250                1255                1260

Lys  Lys  Asn  Trp  Trp  Ser  Ser  Lys  Ser  Lys  Glu  Lys  Lys  His  Ile
     1265                1270                1275

Trp  Phe  Gly  Glu  Thr  Ile  Asn  Gly  Gly  Phe  His  Phe  Ser  Tyr  Gly
     1280                1285                1290

Asp  Asp  Asn  Leu  Ala  Pro  Asn  Thr  Ala  Asn  Val  Gln  Met  Thr  Phe
     1295                1300                1305

Leu  Arg  Leu  Leu  Ser  Thr  Glu  Gly  Ser  Gln  Asn  Ile  Thr  Tyr  His
     1310                1315                1320

Cys  Lys  Asn  Ser  Ile  Ala  Tyr  Leu  Asp  Glu  Ala  Ala  Gly  Asn  Leu
     1325                1330                1335

Lys  Lys  Ala  Leu  Leu  Ile  Gln  Gly  Ser  Asn  Asp  Val  Glu  Ile  Arg
     1340                1345                1350

Ala  Glu  Gly  Asn  Ser  Arg  Phe  Thr  Tyr  Thr  Ala  Leu  Lys  Asp  Gly
     1355                1360                1365

Cys  Thr  Lys  His  Thr  Gly  Lys  Trp  Gly  Lys  Thr  Val  Ile  Glu  Tyr
     1370                1375                1380

Arg  Ser  Gln  Lys  Thr  Ser  Arg  Leu  Pro  Ile  Ile  Asp  Ile  Ala  Pro
     1385                1390                1395

Met  Asp  Ile  Gly  Gly  Pro  Glu  Gln  Glu  Phe  Gly  Val  Asp  Ile  Gly
     1400                1405                1410

Pro  Val  Cys  Phe  Leu
     1415

<210> SEQ ID NO 19
<211> LENGTH: 1487
<212> TYPE: PRT
<213> ORGANISM: Homo sapiens

<400> SEQUENCE: 19

Met  Ile  Arg  Leu  Gly  Ala  Pro  Gln  Thr  Leu  Val  Leu  Leu  Thr  Leu  Leu
1                   5                   10                  15
```

```
Val Ala Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
        195                 200                 205

Arg Gly Pro Pro Gly Pro Ala Gly Ala Pro Gly Pro Gln Gly Phe Gln
    210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
        275                 280                 285

His Arg Gly Tyr Pro Gly Leu Asp Gly Ala Lys Gly Glu Ala Gly Ala
    290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
        355                 360                 365

Gly Ala Pro Gly Ala Lys Gly Glu Ala Gly Pro Thr Gly Ala Arg Gly
    370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
            420                 425                 430

Phe Pro Gly Pro Arg Gly Pro Pro Gly Pro Gln Gly Ala Thr Gly Pro
```

```
                435                 440                 445
Leu Gly Pro Lys Gly Gln Thr Gly Glu Pro Gly Ile Ala Gly Phe Lys
    450                 455                 460
Gly Glu Gln Gly Pro Lys Gly Glu Pro Gly Pro Ala Gly Pro Gln Gly
465                 470                 475                 480
Ala Pro Gly Pro Ala Gly Glu Glu Gly Lys Arg Gly Ala Arg Gly Glu
                485                 490                 495
Pro Gly Gly Val Gly Pro Ile Gly Pro Pro Gly Glu Arg Gly Ala Pro
            500                 505                 510
Gly Asn Arg Gly Phe Pro Gly Gln Asp Gly Leu Ala Gly Pro Lys Gly
            515                 520                 525
Ala Pro Gly Glu Arg Gly Pro Ser Gly Leu Ala Gly Pro Lys Gly Ala
    530                 535                 540
Asn Gly Asp Pro Gly Arg Pro Gly Glu Pro Gly Leu Pro Gly Ala Arg
545                 550                 555                 560
Gly Leu Thr Gly Arg Pro Gly Asp Ala Gly Pro Gln Gly Lys Val Gly
                565                 570                 575
Pro Ser Gly Ala Pro Gly Glu Asp Gly Arg Pro Gly Pro Pro Gly Pro
            580                 585                 590
Gln Gly Ala Arg Gly Gln Pro Gly Val Met Gly Phe Pro Gly Pro Lys
            595                 600                 605
Gly Ala Asn Gly Glu Pro Gly Lys Ala Gly Glu Lys Gly Leu Pro Gly
    610                 615                 620
Ala Pro Gly Leu Arg Gly Leu Pro Gly Lys Asp Gly Glu Thr Gly Ala
625                 630                 635                 640
Ala Gly Pro Pro Gly Pro Ala Gly Pro Ala Gly Glu Arg Gly Glu Gln
                645                 650                 655
Gly Ala Pro Gly Pro Ser Gly Phe Gln Gly Leu Pro Gly Pro Pro Gly
            660                 665                 670
Pro Pro Gly Glu Gly Gly Lys Pro Gly Asp Gln Gly Val Pro Gly Glu
            675                 680                 685
Ala Gly Ala Pro Gly Leu Val Gly Pro Arg Gly Glu Arg Gly Phe Pro
    690                 695                 700
Gly Glu Arg Gly Ser Pro Gly Ala Gln Gly Leu Gln Gly Pro Arg Gly
705                 710                 715                 720
Leu Pro Gly Thr Pro Gly Thr Asp Gly Pro Lys Gly Ala Ser Gly Pro
                725                 730                 735
Ala Gly Pro Pro Gly Ala Gln Gly Pro Pro Gly Leu Gln Gly Met Pro
            740                 745                 750
Gly Glu Arg Gly Ala Ala Gly Ile Ala Gly Pro Lys Gly Asp Arg Gly
            755                 760                 765
Asp Val Gly Glu Lys Gly Pro Glu Gly Ala Pro Gly Lys Asp Gly Gly
    770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
                805                 810                 815
Ala Arg Gly Ala Pro Gly Glu Arg Gly Glu Thr Gly Pro Pro Gly Pro
            820                 825                 830
Ala Gly Phe Ala Gly Pro Pro Gly Ala Asp Gly Gln Pro Gly Ala Lys
            835                 840                 845
Gly Glu Gln Gly Glu Ala Gly Gln Lys Gly Asp Ala Gly Ala Pro Gly
    850                 855                 860
```

```
Pro Gln Gly Pro Ser Gly Ala Pro Gly Pro Gln Pro Thr Gly Val
865                 870                 875                 880

Thr Gly Pro Lys Gly Ala Arg Gly Ala Gln Gly Pro Pro Gly Ala Thr
            885                 890                     895

Gly Phe Pro Gly Ala Ala Gly Arg Val Gly Pro Pro Gly Ser Asn Gly
                900                 905                 910

Asn Pro Gly Pro Pro Gly Pro Pro Gly Pro Ser Gly Lys Asp Gly Pro
            915                 920                 925

Lys Gly Ala Arg Gly Asp Ser Gly Pro Pro Gly Arg Ala Gly Glu Pro
        930                 935                 940

Gly Leu Gln Gly Pro Ala Gly Pro Pro Gly Glu Lys Gly Glu Pro Gly
945                 950                 955                 960

Asp Asp Gly Pro Ser Gly Ala Glu Gly Pro Pro Gly Pro Gln Gly Leu
                965                 970                 975

Ala Gly Gln Arg Gly Ile Val Gly Leu Pro Gly Gln Arg Gly Glu Arg
            980                 985                 990

Gly Phe Pro Gly Leu Pro Gly Pro Ser Gly Glu Pro Gly Lys Gln Gly
                995                 1000                1005

Ala Pro Gly Ala Ser Gly Asp Arg Gly Pro Pro Gly Pro Val Gly
1010                1015                1020

Pro Pro Gly Leu Thr Gly Pro Ala Gly Glu Pro Gly Arg Glu Gly
1025                1030                1035

Ser Pro Gly Ala Asp Gly Pro Pro Gly Arg Asp Gly Ala Ala Gly
1040                1045                1050

Val Lys Gly Asp Arg Gly Glu Thr Gly Ala Val Gly Ala Pro Gly
1055                1060                1065

Ala Pro Gly Pro Pro Gly Ser Pro Gly Pro Ala Gly Pro Thr Gly
1070                1075                1080

Lys Gln Gly Asp Arg Gly Glu Ala Gly Ala Gln Gly Pro Met Gly
1085                1090                1095

Pro Ser Gly Pro Ala Gly Ala Arg Gly Ile Gln Gly Pro Gln Gly
1100                1105                1110

Pro Arg Gly Asp Lys Gly Glu Ala Gly Glu Pro Gly Glu Arg Gly
1115                1120                1125

Leu Lys Gly His Arg Gly Phe Thr Gly Leu Gln Gly Leu Pro Gly
1130                1135                1140

Pro Pro Gly Pro Ser Gly Asp Gln Gly Ala Ser Gly Pro Ala Gly
1145                1150                1155

Pro Ser Gly Pro Arg Gly Pro Pro Gly Pro Val Gly Pro Ser Gly
1160                1165                1170

Lys Asp Gly Ala Asn Gly Ile Pro Gly Pro Ile Gly Pro Pro Gly
1175                1180                1185

Pro Arg Gly Arg Ser Gly Glu Thr Gly Pro Ala Gly Pro Pro Gly
1190                1195                1200

Asn Pro Gly Pro Pro Gly Pro Pro Gly Pro Pro Gly Pro Gly Ile
1205                1210                1215

Asp Met Ser Ala Phe Ala Gly Leu Gly Pro Arg Glu Lys Gly Pro
1220                1225                1230

Asp Pro Leu Gln Tyr Met Arg Ala Asp Gln Ala Ala Gly Gly Leu
1235                1240                1245

Arg Gln His Asp Ala Glu Val Asp Ala Thr Leu Lys Ser Leu Asn
1250                1255                1260
```

-continued

Asn Gln Ile Glu Ser Ile Arg Ser Pro Glu Gly Ser Arg Lys Asn
    1265                1270                1275

Pro Ala Arg Thr Cys Arg Asp Leu Lys Leu Cys His Pro Glu Trp
    1280                1285                1290

Lys Ser Gly Asp Tyr Trp Ile Asp Pro Asn Gln Gly Cys Thr Leu
    1295                1300                1305

Asp Ala Met Lys Val Phe Cys Asn Met Glu Thr Gly Glu Thr Cys
    1310                1315                1320

Val Tyr Pro Asn Pro Ala Asn Val Pro Lys Lys Asn Trp Trp Ser
    1325                1330                1335

Ser Lys Ser Lys Glu Lys Lys His Ile Trp Phe Gly Glu Thr Ile
    1340                1345                1350

Asn Gly Gly Phe His Phe Ser Tyr Gly Asp Asp Asn Leu Ala Pro
    1355                1360                1365

Asn Thr Ala Asn Val Gln Met Thr Phe Leu Arg Leu Leu Ser Thr
    1370                1375                1380

Glu Gly Ser Gln Asn Ile Thr Tyr His Cys Lys Asn Ser Ile Ala
    1385                1390                1395

Tyr Leu Asp Glu Ala Ala Gly Asn Leu Lys Lys Ala Leu Leu Ile
    1400                1405                1410

Gln Gly Ser Asn Asp Val Glu Ile Arg Ala Glu Gly Asn Ser Arg
    1415                1420                1425

Phe Thr Tyr Thr Ala Leu Lys Asp Gly Cys Thr Lys His Thr Gly
    1430                1435                1440

Lys Trp Gly Lys Thr Val Ile Glu Tyr Arg Ser Gln Lys Thr Ser
    1445                1450                1455

Arg Leu Pro Ile Ile Asp Ile Ala Pro Met Asp Ile Gly Gly Pro
    1460                1465                1470

Glu Gln Glu Phe Gly Val Asp Ile Gly Pro Val Cys Phe Leu
    1475                1480                1485

<210> SEQ ID NO 20
<211> LENGTH: 268
<212> TYPE: PRT
<213> ORGANISM: Homo sapiens

<400> SEQUENCE: 20

Met Ser Ala Phe Ala Gly Leu Gly Pro Arg Glu Lys Gly Pro Asp Pro
1               5                   10                  15

Leu Gln Tyr Met Arg Ala Asp Gln Ala Ala Gly Gly Leu Arg Gln His
            20                  25                  30

Asp Ala Glu Val Asp Ala Thr Leu Lys Ser Leu Asn Asn Gln Ile Glu
        35                  40                  45

Ser Ile Arg Ser Pro Glu Gly Ser Arg Lys Asn Pro Ala Arg Thr Cys
    50                  55                  60

Arg Asp Leu Lys Leu Cys His Pro Glu Trp Lys Ser Gly Asp Tyr Trp
65                  70                  75                  80

Ile Asp Pro Asn Gln Gly Cys Thr Leu Asp Ala Met Lys Val Phe Cys
                85                  90                  95

Asn Met Glu Thr Gly Glu Thr Cys Val Tyr Pro Asn Pro Ala Asn Val
            100                 105                 110

Pro Lys Lys Asn Trp Trp Ser Ser Lys Ser Lys Glu Lys Lys His Ile
        115                 120                 125

Trp Phe Gly Glu Thr Ile Asn Gly Gly Phe His Phe Ser Tyr Gly Asp
    130                 135                 140

Asp Asn Leu Ala Pro Asn Thr Ala Asn Val Gln Met Thr Phe Leu Arg
145                 150                 155                 160

Leu Leu Ser Thr Glu Gly Ser Gln Asn Ile Thr Tyr His Cys Lys Asn
            165                 170                 175

Ser Ile Ala Tyr Leu Asp Glu Ala Ala Gly Asn Leu Lys Lys Ala Leu
        180                 185                 190

Leu Ile Gln Gly Ser Asn Asp Val Glu Ile Arg Ala Glu Gly Asn Ser
            195                 200                 205

Arg Phe Thr Tyr Thr Ala Leu Lys Asp Gly Cys Thr Lys His Thr Gly
        210                 215                 220

Lys Trp Gly Lys Thr Val Ile Glu Tyr Arg Ser Gln Lys Thr Ser Arg
225                 230                 235                 240

Leu Pro Ile Ile Asp Ile Ala Pro Met Asp Ile Gly Pro Glu Gln
            245                 250                 255

Glu Phe Gly Val Asp Ile Gly Pro Val Cys Phe Leu
            260                 265

<210> SEQ ID NO 21
<211> LENGTH: 2
<212> TYPE: PRT
<213> ORGANISM: Artificial Sequence
<220> FEATURE:
<223> OTHER INFORMATION: linker monomer

<400> SEQUENCE: 21

Gly Ser
1

<210> SEQ ID NO 22
<211> LENGTH: 3
<212> TYPE: PRT
<213> ORGANISM: Artificial Sequence
<220> FEATURE:
<223> OTHER INFORMATION: linker monomer

<400> SEQUENCE: 22

Gly Gly Ser
1

<210> SEQ ID NO 23
<211> LENGTH: 4
<212> TYPE: PRT
<213> ORGANISM: Artificial Sequence
<220> FEATURE:
<223> OTHER INFORMATION: linker monomer

<400> SEQUENCE: 23

Gly Gly Gly Ser
1

<210> SEQ ID NO 24
<211> LENGTH: 5
<212> TYPE: PRT
<213> ORGANISM: Artificial Sequence
<220> FEATURE:
<223> OTHER INFORMATION: linker monomer

<400> SEQUENCE: 24

Gly Gly Gly Gly Ser
1               5